(12) United States Patent
Park et al.

(10) Patent No.: US 12,228,509 B2
(45) Date of Patent: Feb. 18, 2025

(54) MICROORGANISM INFORMATION PROVIDING DEVICE AND METHOD

(71) Applicants: THE WAVE TALK, INC., Daejeon (KR); KOREA ADVANCED INSTITUTE OF SCIENCE AND TECHNOLOGY, Daejeon (KR)

(72) Inventors: YongKeun Park, Daejeon (KR); KyeoReh Lee, Chungcheongnam-do (KR); Seungwoo Shin, Busan (KR); Geon Kim, Daejeon (KR); Young Dug Kim, Gyeonggi-do (KR)

(73) Assignees: THE WAVE TALK, INC., Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 951 days.

(21) Appl. No.: 17/273,631

(22) PCT Filed: Sep. 6, 2019

(86) PCT No.: PCT/KR2019/011559
§ 371 (c)(1),
(2) Date: Mar. 4, 2021

(87) PCT Pub. No.: WO2020/050687
PCT Pub. Date: Mar. 12, 2020

(65) Prior Publication Data
US 2021/0340591 A1    Nov. 4, 2021

(30) Foreign Application Priority Data

Sep. 7, 2018 (KR) .................. 10-2018-0107292
Apr. 17, 2019 (KR) .................. 10-2019-0045142

(51) Int. Cl.
*G16B 40/00* (2019.01)
*C12Q 1/06* (2006.01)
(Continued)

(52) U.S. Cl.
CPC .......... *G01N 21/4788* (2013.01); *C12Q 1/06* (2013.01); *G01N 21/47* (2013.01); *G06N 20/00* (2019.01);
(Continued)

(58) Field of Classification Search
CPC . C12Q 1/06; C12Q 1/04; G01N 21/47; G01N 15/06; G01N 2201/1296;
(Continued)

(56) References Cited

U.S. PATENT DOCUMENTS 10,521,910 B2 * 12/2019 Wiles ............... C12M 41/46
10,692,216 B2 *  6/2020 Wiles ............... C12M 23/10
(Continued)

FOREIGN PATENT DOCUMENTS

KR    2012-0036727 A    4/2012
KR    2013-0038334 A    4/2013
(Continued)

OTHER PUBLICATIONS

International Search Report and Written Opinion mailed in International Patent Application No. PCT/KR2019/011559, filed Sep. 6, 2019, 13 pages.

*Primary Examiner* — Isiaka O Akanbi
(74) *Attorney, Agent, or Firm* — Kilpatrick Townsend & Stockton LLP

(57) ABSTRACT

According to an embodiment of the present disclosure, provided is an apparatus for providing microorganism information, including: a receiving unit configured to receive a plurality of images obtained by photographing in time series an outgoing wave emitted from a sample; a detecting unit
(Continued)

configured to extract a feature of a change over time from the plurality of images obtained by photographing in time series; a learning unit configured to machine-learn classification criteria based on the extracted feature; and a determining unit configured to classify the type or concentration of a microorganism included in the sample based on the classification criteria, wherein each of the plurality of images includes speckle information generated by multiple scattering by the microorganism due to waves incident on the sample.

16 Claims, 15 Drawing Sheets

(51) Int. Cl.
    *G01N 21/47*     (2006.01)
    *G06N 20/00*     (2019.01)
    *G06V 10/764*     (2022.01)
    *G06V 10/82*     (2022.01)
    *G06V 20/69*     (2022.01)

(52) U.S. Cl.
    CPC ............ *G06V 10/764* (2022.01); *G06V 10/82* (2022.01); *G06V 20/695* (2022.01); *G06V 20/698* (2022.01); *G16B 40/00* (2019.02)

(58) Field of Classification Search
CPC .... G01N 2021/479; G06N 20/00; G06N 3/08; G06V 10/82; G16B 40/00; G16H 30/40
USPC .................................. 356/446, 338, 402, 51
See application file for complete search history.

(56) References Cited

U.S. PATENT DOCUMENTS

| | | | |
|---|---|---|---|
| 2013/0109051 A1* | 5/2013 | Li | G06T 7/0012 435/288.7 |
| 2014/0219538 A1* | 8/2014 | Guthrie | G06V 20/69 382/133 |
| 2015/0347817 A1 | 12/2015 | Valvik et al. | |
| 2016/0110584 A1* | 4/2016 | Remiszewski | G06V 20/69 382/133 |
| 2017/0138923 A1* | 5/2017 | Park | G01N 15/06 |
| 2018/0090299 A1* | 3/2018 | Nakayamada | H01J 37/3174 |

FOREIGN PATENT DOCUMENTS

| | | |
|---|---|---|
| KR | 2014-0045923 A | 4/2014 |
| KR | 2017-0118032 A | 10/2017 |
| KR | 2018-0053984 A | 5/2018 |
| WO | 2017-086719 A | 5/2017 |

* cited by examiner

FIG. 11

|  | | Prediction → | | | | | | | | | | | |
|---|---|---|---|---|---|---|---|---|---|---|---|---|---|
| PBS | | 132 | 0 | 0 | 0 | 0 | 0 | 0 | 0 | 0 | 0 | 0 | 0 |
| B. subtilis | ×10³ | 0 | 132 | 0 | 0 | 0 | 0 | 0 | 0 | 0 | 0 | 0 | 0 |
|  | ×10⁵ | 0 | 0 | 132 | 0 | 0 | 0 | 0 | 0 | 0 | 0 | 0 | 0 |
|  | ×10⁷ | 0 | 0 | 0 | 132 | 0 | 0 | 0 | 0 | 0 | 0 | 0 | 0 |
| E. coli | | 0 | 0 | 0 | 0 | 132 | 0 | 0 | 0 | 0 | 0 | 0 | 0 |
|  | | 0 | 0 | 0 | 0 | 0 | 132 | 0 | 0 | 0 | 0 | 0 | 0 |
|  | | 0 | 0 | 0 | 0 | 0 | 0 | 132 | 0 | 0 | 0 | 0 | 0 |
| P. aeruginosa | | 2 | 0 | 0 | 0 | 0 | 0 | 0 | 130 | 0 | 0 | 0 | 0 |
|  | | 1 | 0 | 0 | 0 | 0 | 0 | 0 | 0 | 131 | 0 | 0 | 0 |
|  | | 0 | 0 | 0 | 0 | 0 | 0 | 0 | 0 | 0 | 132 | 0 | 0 |
| S. aureus | | 6 | 0 | 0 | 0 | 2 | 0 | 0 | 0 | 0 | 0 | 124 | 0 | 0 |
|  | | 0 | 0 | 0 | 0 | 0 | 3 | 0 | 0 | 0 | 0 | 0 | 129 | 0 |
|  | | 0 | 0 | 0 | 0 | 0 | 0 | 0 | 0 | 0 | 0 | 0 | 0 | 132 |

Ground truth ↓

MICROORGANISM INFORMATION PROVIDING DEVICE AND METHOD

TECHNICAL FIELD

Embodiments of the present disclosure relates to an apparatus and method for providing microorganism information.

BACKGROUND ART

Various pathogenic microorganisms such as bacteria, fungi, and viruses appear and inhabit in the blood, body fluids and tissues of the human body, causing infectious diseases. In recent years, pathogenic infections have emerged greatly in society, and the frequency thereof is gradually increasing. Pathogenic infections, which have begun to become a legal problem in the medical field, can kill people if not treated with proper treatments. Accordingly, early diagnosis and rapid treatment without complications are required. Therefore, there is a need to develop an accurate and rapid diagnostic method of these pathogenic microorganisms.

Furthermore, recently, the misuse of antibiotics has led to a decrease in the culture rate of bacteria, and since the use of immunosuppressants following the transplant is increased, the use of drugs is increased due to anti-cancer treatment, and increased AIDS has led to a variety of bacteria causing the increased number of bacteria, diagnostic methods for diagnosing existing infectious diseases such as embryo tests are increasingly facing difficulties.

DESCRIPTION OF EMBODIMENTS

Technical Problem

Embodiments of the present disclosure provide an apparatus and method for providing microorganism information by classifying the type and concentration of a microorganism in a sample using machine-learning.

Solution To Problem

According to an embodiment of the present disclosure, provided is an apparatus for providing microorganism information, including: a receiving unit configured to receive a plurality of images obtained by photographing in time series an outgoing wave emitted from a sample; a detecting unit configured to extract a feature of a change over time from the plurality of images obtained by photographing in time series; a learning unit configured to machine-learn classification criteria based on the extracted feature; and a determining unit configured to classify the type or concentration of a microorganism included in the sample based on the classification criteria, wherein each of the plurality of images includes speckle information generated by multiple scattering by the microorganisms due to waves incident on the sample.

Advantageous Effects of Disclosure

According to the apparatus and method for providing microorganism information according to embodiments of the present disclosure, a feature of a change of a speckle over time is extracted and is used for training to obtain classification criteria for classifying the type or concentration of a microorganism. Accordingly, the type or concentration of a microorganism in a sample can be quickly and accurately identified without a separate chemical method.

BRIEF DESCRIPTION OF DRAWINGS

FIG. 11 is a graph in which expected microorganism information, which is obtained using a method of providing microorganism information according to an embodiment of the present disclosure, is compared with actual microorganism information.

BEST MODE

Figure 1:
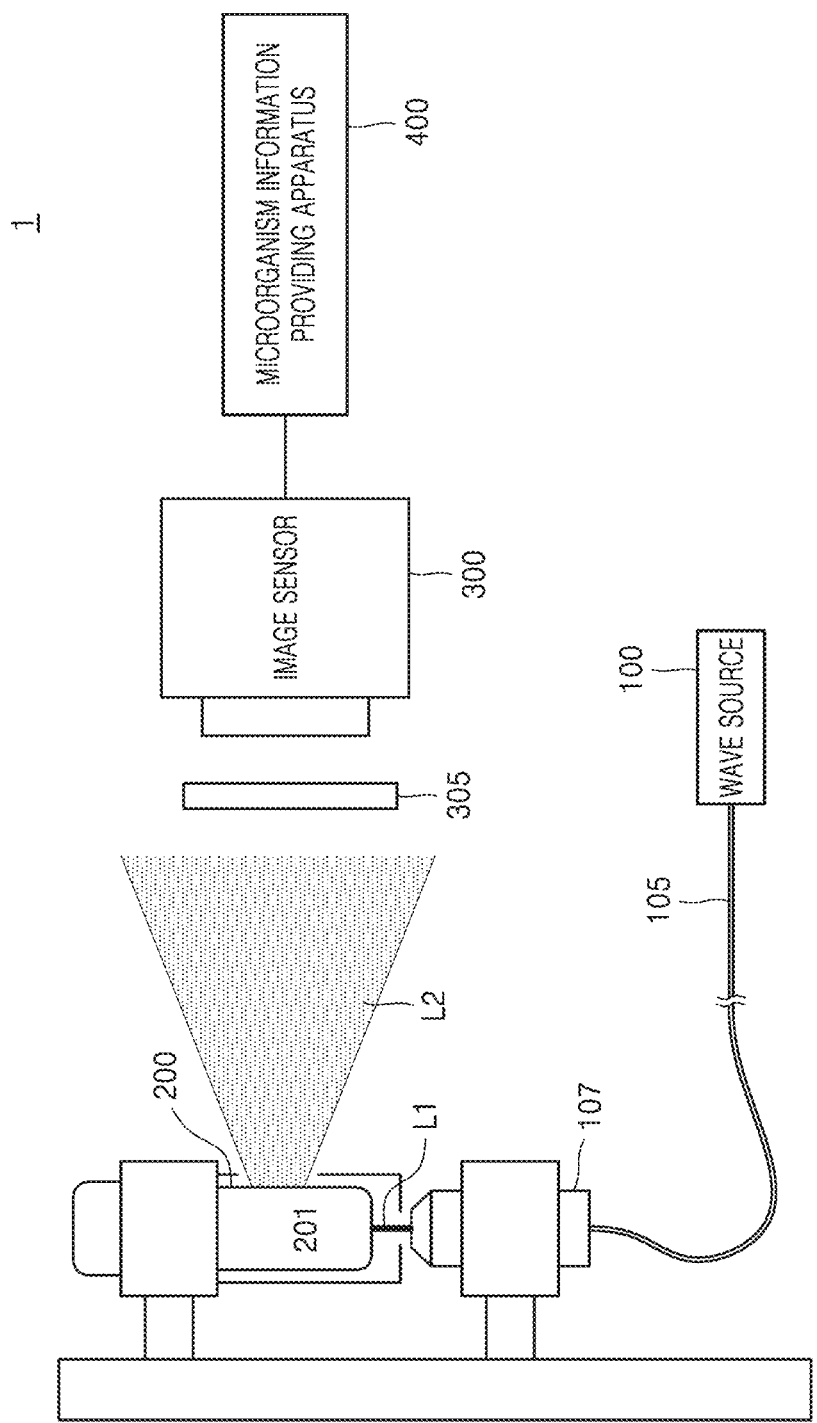
FIG. 1 is a schematic diagram of a system for providing microorganism information according to an embodiment of the present disclosure.

According to an embodiment of the present disclosure, provided is an apparatus for providing microorganism information, the apparatus including: a receiving unit configured to receive a plurality of images obtained by photographing an outgoing wave emitted from a sample in time series; a detecting unit configured to extract a feature of a change over time from the plurality of images obtained by photographing in time series; a learning unit configured to machine-learn classification criteria based on the extracted feature; and a determining unit configured to classify the type or concentration of a microorganism included in the sample based on the classification criteria, wherein each of the plurality of images includes speckle information generated by multiple scattering by the microorganism due to waves incident on the sample.

In an embodiment of the present disclosure, the learning unit may learn the classification criteria by using a convolutional neural network (CNN).

In an embodiment of the present disclosure, the learning unit may perform convolution arithmetic using a convolution kernel having a size smaller than the size of one speckle.

In an embodiment of the present disclosure, when the size of one speckle corresponds to m pixels, the learning unit may perform convolution arithmetic using an n×n-sized convolution kernel having the size less than m.

In an embodiment of the present disclosure, the stride of the convolution arithmetic may correspond to the n value.

In an embodiment of the present disclosure, the convolution kernel may include kernel feature maps corresponding to or greater than the number of images.

In an embodiment of the present disclosure, the learning unit may perform convolution arithmetic using a kernel set including a plurality of convolution kernels corresponding to the number of output channels.

In an embodiment of the present disclosure, the number of output channels by the convolution arithmetic may correspond to the number of the plurality of images.

In an embodiment of the present disclosure, the learning unit may learn the classification criteria based on the temporal correlation of the plurality of images.

In an embodiment of the present disclosure, the classification criteria may be learned using, among the features, one of a change in a shape of a speckle pattern, a temporal correlation coefficient calculated based on an intensity of light of the speckle pattern, and a change in a standard deviation value of the intensity of light of the speckle pattern.

In an embodiment of the present disclosure, the standard deviation value and the concentration of the microorganism may have a linear relationship.

According to an embodiment of the present disclosure, provided is a method of providing microorganism information, the method includes: receiving a plurality of training images obtained by previously photographing in time series outgoing waves emitted by irradiating waves to a sample of which a type or concentration of a microorganism has been known; machine-learning classification criteria based on a feature of a change over time from the training images obtained by previously photographing in time series; receiving a plurality of images obtained by photographing in time series outgoing waves emitted by irradiating waves to a new sample; and classifying the type or the concentration of microorganisms included in the new sample based on the images and the classification criteria, wherein each of the training images or each of the images includes speckle information generated by multiple scattering by the microorganisms due to waves incident on the new sample.

In an embodiment of the present disclosure, in the machine-learning of the classification criteria, CNN is used to learn the classification criteria.

In an embodiment of the present disclosure, the machine-learning of the classification criteria may perform convolution arithmetic using a convolution kernel having a size smaller than the size of one speckle.

In an embodiment of the present disclosure, when the size of one speckle corresponds to m pixels, the machine-learning of the classification criteria may perform convolution arithmetic using an n×n-sized convolution kernel having the size less than m.

In an embodiment of the present disclosure, the stride of the convolution arithmetic may correspond to the n value.

In an embodiment of the present disclosure, the convolution kernel may include kernel feature maps corresponding to or greater than the number of images.

In an embodiment of the present disclosure, the machine-learning of the classification criteria may perform convolution arithmetic using a kernel set including a plurality of convolution kernels corresponding to the number of output channels.

In an embodiment of the present disclosure, the number of the output channels by the convolution arithmetic may correspond to the number of the plurality of images.

In an embodiment of the present disclosure, the learning unit may learn the classification criteria based on the temporal correlation of the plurality of images.

In an embodiment of the present disclosure, the classification criteria may be learned using, among the features, one of a change in a shape of a speckle pattern, a temporal correlation coefficient calculated based on an intensity of light of the speckle pattern, and a change in a standard deviation value of the intensity of light of the speckle pattern.

In an embodiment of the present disclosure, the standard deviation value and the concentration of the microorganism may have a linear relationship.

An embodiment of the present disclosure provides a system for providing microorganism information, the system including a sample unit accommodating a sample, a wave source irradiating waves to the sample, an image sensor obtaining a plurality of images by photographing in time series an outgoing wave emitted from the sample, and a microorganism information providing apparatus for providing microorganism information including the type or concentration of a microorganism by using the images obtained by photographing in time series, wherein the microorganism information providing apparatus includes a receiving unit receiving the images, a detecting unit extracting a feature of a change over time from the images obtained in time series, a learning unit machine-learning classification criteria based on the feature which is extracted, and a determining unit identifying the type or concentration of a microorganism contained in the sample based on the classification criteria, wherein each of the plurality of images includes speckle information generated by multiple scattering caused by the microorganism due to a wave entering into the sample.

According to another aspect of the present disclosure, provided is an optical detection system, including a sample unit accommodating a sample, a wave source irradiating waves to the sample unit, an optical unit disposed on a path of an outgoing wave emitted from the sample unit, and including a first spatial light modulator modulating a portion of the outgoing wave into a first wave and a second spatial light modulator modulating a portion of the outgoing wave into a second wave; a lens unit focusing the first wave and the second wave emitted from the optical unit; and a detecting unit detecting a focused wave focused by the lens unit, wherein the first spatial light modulator and the second spatial light modulator modulate the outgoing waves such that destructive interference occurs between the first wave and the second wave with respect to the sample under a known condition.

In an embodiment of the present disclosure, the outgoing wave may include a speckle pattern generated by multiple scattering from the sample.

In an embodiment of the present disclosure, the sample unit may further include a multiple-scattering amplification unit to amplify the number of times that waves irradiated onto the sample are multiple-scattered.

In an embodiment of the present disclosure, the detecting unit may detect whether there is an impurity in the sample according to whether the focused wave is sensed.

According to another aspect of the present disclosure, provided is an optical detection system including a sample unit accommodating a sample, a wave source irradiating waves to the sample unit, and an optical unit disposed on a path of an outgoing wave emitted from the sample unit and including a first spatial light modulator modulating a portion of the outgoing wave into a first wave, a lens unit focusing the first wave emitted from the optical unit and a second wave that is a portion of the outgoing wave, and a detecting unit detecting a focused wave focused by the lens unit, wherein the first spatial light modulator modulates the outgoing wave such that destructive interference occurs between the first wave and the second wave with respect to the sample under a known condition.

In an embodiment of the present disclosure, the outgoing wave may include a speckle pattern generated by multiple scattering from the sample.

In an embodiment of the present disclosure, the sample unit may further include a multiple-scattering amplification unit to amplify the number of times that waves irradiated onto the sample are multiple-scattered.

In an embodiment of the present disclosure, the detecting unit may detect whether there is an impurity in the sample according to whether the focused wave is sensed.

Other aspects, features, and advantages other than the above-described features will be apparent from the following drawings, claims, and detailed descriptions of the disclosure.

Mode of Disclosure

Hereinafter, the following embodiments will be described in detail with reference to the accompanying drawings, and in the following description with reference to the drawings, like or corresponding components are denoted by like reference numerals, and redundant descriptions thereof will be omitted.

Since the present embodiments may apply various changes, specific embodiments are illustrated in the drawings and will be described in detail in the detailed description. The effects and features of the embodiments and methods of achieving the same will become apparent with reference to the following descriptions in detail with reference to the drawings. However, the embodiments are not limited to the embodiments described below, but may be implemented in various forms.

In the following embodiments, the terms "first" and "second" are not limited and are used to distinguish one component from other components.

In the following embodiments, a singular expression includes a plurality of expressions unless defined otherwise in context.

In the following embodiments, the terms such as "include" or "have" indicate that a feature or a component described in the specification is present, and do not preclude a possibility that one or more other features or components are added.

In the following embodiments, when a unit, an area, a component, etc. is located on or above another part, the present disclosure includes not only a case where the unit, the area, the component, etc. are located directly above the other part, but also a case where other units, other areas, other component, etc. may be located therebetween.

In the following embodiments, unless the terms "connecting" or "coupling" are clearly different in context, the terms "connecting" or "coupling" do not necessarily mean direct and/or fixed connection or coupling of two members, but do not exclude a member located between the two members.

It means that a feature or a component described in the specification is present, and does not preclude in advance a possibility that one or more other features or components are added.

In the drawings, for convenience of description, the size of the components may be exaggerated or reduced. For example, the size and thickness of each configuration shown in the drawings are arbitrarily shown for convenience of description, and thus the following embodiments are not necessarily limited to those shown in the drawings.

FIG. 1 is a diagram schematically illustrating a microorganism information providing system 1 according to an embodiment of the present disclosure.

Referring to FIG. 1, the microorganism information providing system 1 according to an embodiment of the present disclosure includes a wave source 100, a sample unit 200, an image sensor 300, and a microorganism information providing apparatus 400.

The wave source 100 may irradiate a wave L1 toward a sample 201. The wave source 100 may be any type of source devices capable of generating a wave, and may be, for example, a laser capable of irradiating light having a specific wavelength band. The present disclosure is not limited to the type of a wave source, but hereinafter, for convenience of description, a laser will be mainly described.

For example, in order to form a speckle in a sample, a laser having a good coherence may be used as the wave source 100. In this case, as a spectral bandwidth of a wave source, determining the coherence of a laser wave source, is reduced, the measurement accuracy may be increased. That is, as a coherence length increases, measurement accuracy may increase. Accordingly, a laser beam, of which the spectral bandwidth is less than the predefined reference bandwidth, may be used as the wave source 100, and the measurement accuracy may be increased as the spectral bandwidth of the wave source is shorter than the reference bandwidth. For example, the spectral bandwidth of the wave source 100 may be set to maintain Equation 1.

$$\text{Spectral bandwidth} < 5 \text{ nm} \qquad \text{Equation 1}$$

According to Equation 1, in order to measure the pattern change of the laser speckle, the spectral bandwidth of the wave source 100 may be maintained to be less than 5 nm when light is irradiated into the sample 201 at every reference time.

In an embodiment, as illustrated in FIG. 1, the wave source 100 may be disposed outside the sample unit 200 to irradiate the wave L1 toward the sample unit 200. In this case, the wave source 100 may be disposed adjacent to the sample unit 200 to directly irradiate the wave L1 toward the sample unit 200, or may be disposed to be spaced apart from the sample unit 200 to irradiate the wave L1 to the sample unit 200 through an optical fiber 105.

Since the optical fiber 105 transfers only a specific wavelength, noise of the wave L1 transferred from the wave source 100 may be removed, and when the wave L1 is emitted, a beam size may be enlarged and provided to the collimator 107.

The sample unit 200 may accommodate the sample 201 to be measured. The sample 201 may be accommodated through a sample placing element such as a container or a pipe, and may be accommodated in a static state. According to an embodiment, as illustrated in FIG. 1, the sample unit 200 may contain a sample 201 stabilized due to no fluidity obtained by using a container. According to another embodiment, although not shown, the sample unit 200 may accommodate the sample 201 having fluidity by using a pipe. In this case, when the sample unit 200 uses a pipe, the sample 201 may be a liquid, and the sample unit 200 may circulate the sample 201 one or more times along the entire flow path including the pipe to form a static state of the sample 201 in the pipe.

The sample unit 200 may further include a multiple-scattering amplification unit. The multiple-scattering amplification unit may reflect at least a portion of the outgoing wave L2 emitted from the sample 201 to the sample 201 to amplify the number of multiple-scatterings in the sample 201. The multiple-scattering amplification unit may include a multiple scattering material. For example, the multiple scattering material may include titanium oxide ($TiO_2$), and the multiple-scattering amplification unit may reflect at least a portion of an incident wave L1 entering the multiple-scattering amplification unit.

The multiple-scattering amplification unit may be disposed adjacent to the sample 201, and may allow the outgoing wave L2 emitted by being multiple-scattered from the sample 201 to reciprocate at least once in a space between the sample 201 and the multiple-scattering amplification unit. The multiple-scattering amplification unit may be disposed on the path of the wave, and may be disposed on each of the path of the incident wave L1 and the path of the outgoing wave L2.

In an embodiment, instead of the embodiment in which the sample unit 200 includes a multiple scattering amplification part as a separate component, the multiple-scattering amplification unit may be formed as a multiple-scattering amplification area by coating a multiple scattering amplification material on the surface of the body of the sample unit 200 accommodating the sample 201. In an embodiment, the sample unit 200 may be configured such that the multiple scattering material is included in the sample 201. The multiple scattering amplification area may scatter at least a portion of waves which enter the inner space of the sample unit 200 and then exit through the sample 201, back into the sample 201 again. The scattered wave is again emitted to the other side through the sample 201 and scattered, and through this process, the number of multiple scattering in the sample 201 may be increased. The multiple-scattering amplification area may be formed in at least a portion of the path through which a wave passes, and may be disposed in the entire area excluding a portion of the area which the wave exits and a portion of the area which the wave enters.

The image sensor 300 is disposed on a path through which the outgoing wave L2 passes, and may obtain a plurality of images of the outgoing wave L2 emitted from the sample 201 by photographing in time series. The image sensor 300 may include a sensing member corresponding to a type of the wave source 100, and for example, when a light source in a visible wavelength band is used, a CCD camera, which is a photographing device, may be used.

Herein, each of the plurality of images may include speckle information that is generated by multiple scattering by microorganisms due to the incident wave L1 entering the sample 201. In other words, the image sensor 300 may detect laser speckle generated when the incident wave L1, which has been irradiated, is multiple-scattered in the sample 201 at a preset time. Here, the "time" used herein refers to any one moment of continuous time flow, and the times may be previously set at the same time intervals, but are not limited thereto, and may be previously set at any time intervals.

The image sensor 300 may capture a first image including first speckle information at least at a first time, and a second image including second speckle information at a second time, and may provide the same to the microorganism information providing apparatus 400. Meanwhile, the first time and the second time are only an example selected for convenience of description, and the image sensor 300 may capture a plurality of images at a plurality of times greater than the first time and the second time. The image sensor 300 includes a polarizer 305 in a path through which the outgoing wave L2 passes, thereby maximizing interference efficiency for forming a speckle and removing unnecessary external reflection light.

The image sensor 300 may be spaced apart from the sample unit 200 by a predetermined distance such that a size d of one pixel of the image sensor 300 is equal to or smaller than a grain size of a speckle pattern. For example, the image sensor 300 may be disposed on a path through which the outgoing wave L2 passes to satisfy the condition of Equation 2.

$$d \leq \text{speckle grain size} \qquad \text{Equation 2}$$

As shown in Equation 2, the size d of one pixel of the image sensor 300 may be equal to or less than a grain size of a speckle pattern, but when the size of the pixel is too small, undersampling may occur, and thus, it may be difficult to use a pixel resolution. Accordingly, the image sensor 300 may be disposed such that up to five pixels are located corresponding to a speckle grain size in order to achieve an effective signal-to-noise ratio (SNR).

Meanwhile, the microorganism information providing apparatus 400 may receive a plurality of images from the image sensor 300, perform machine-learning using the images, and then perform a function of distinguishing the type or concentration of a microorganism in the sample 201. Hereinafter, the microorganism information providing apparatus 400 according to the present disclosure will be described in detail with reference to FIGS. 2 and 3.

Figure 2:
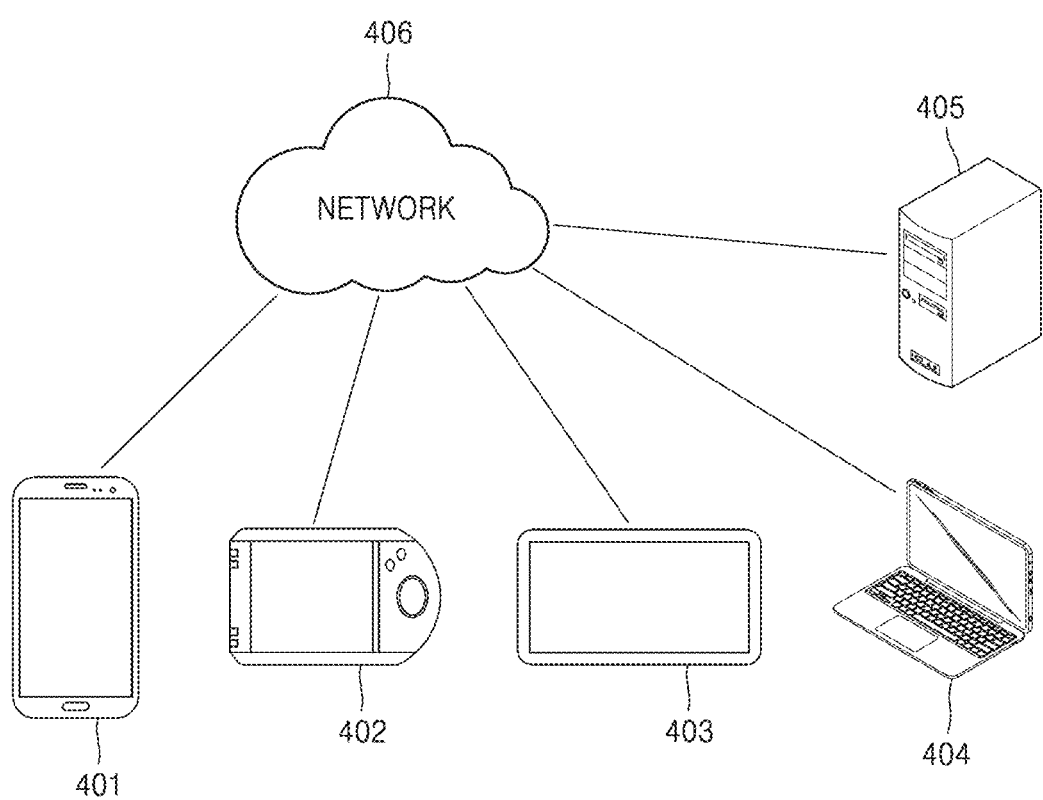
FIG. 2 shows an example of a network environment according to an embodiment of the present disclosure.

FIG. 2 shows an example of a network environment according to an embodiment of the present disclosure;

Referring to FIG. 2, the network environment includes a plurality of user terminals 401, 402, 403, and 404, a server 405, and a network 406. Here, the microorganism information providing apparatus 400 may be a server or a user terminal. The embodiment illustrated in FIG. 2 is an example only for describing the present disclosure, and the number of user terminals or the number of servers is not limited to FIG. 2.

The plurality of user terminals 401, 402, 403, and 404 may be fixed terminals implemented as computer devices, or mobile terminals. When the microorganism information providing apparatus 400 is the server 405, the plurality of user terminals 401, 402, 403, and 404 may be terminals of a manager controlling the server 405. Examples of the plurality of user terminals 401, 402, 403, and 404 include a smartphone, a mobile phone, a navigation device, a computer, a notebook computer, a digital broadcasting terminal, a personal digital assistant (PDA), a portable multimedia player (PMP), and a tablet PC. For example, the user terminal 401 may communicate with the other user terminals 402, 403, and 404 and/or the server 405 through the network 406 in a wireless or wired communication manner. In an embodiment, the plurality of user terminals 401, 402, 403, and 404 may include the image sensor 300 described above, and may transmit a plurality of obtained images to the server 405 through the network 406.

The communication method is not limited, and may include a near field communication among devices, as well as a communication method using a communication network that may be included in the network 406 (for example, a mobile communication network, a wired Internet, a wireless Internet, and a broadcasting network). For example, the network 406 may include at least one network of personal area network (PAN), local area network (LAN), capus area network (CAN), metropolitan area network (MAN), wide area network (WAN), metropolitan area network (MAN), wide area network (WAN), broadband network (BBN), and the Internet. In an embodiment, the network 406 may include any one or more of a bus network, a star network, a ring network, a mesh network, a star-bus network, a network topology including a tree, or a hierarchical network, etc, but is not limited thereto.

The server 405 may be implemented as a computer device or a plurality of computer devices that communicate with the plurality of user terminals 401, 402, 403, and 404 through the network 406 to provide commands, codes, files, contents, services, etc.

For example, the server 405 may provide a file for installing an application to the user terminal 401 connected through the network 406. In this case, the user terminal 401 may install the application by using the file provided from the server. In addition, under the control of an operating system (OS) including the user terminal 401 and at least one program (for example, a browser or an installed application), the user terminal 401 may access the server 405 and receive a service or content provided by the server 405. In an embodiment, the server 405 may set a communication session for data transmission and reception, and, through the set communication session, the server 405 may route data transmission and reception among the plurality of user terminals 401, 402, 403, and 404.

Figure 3:
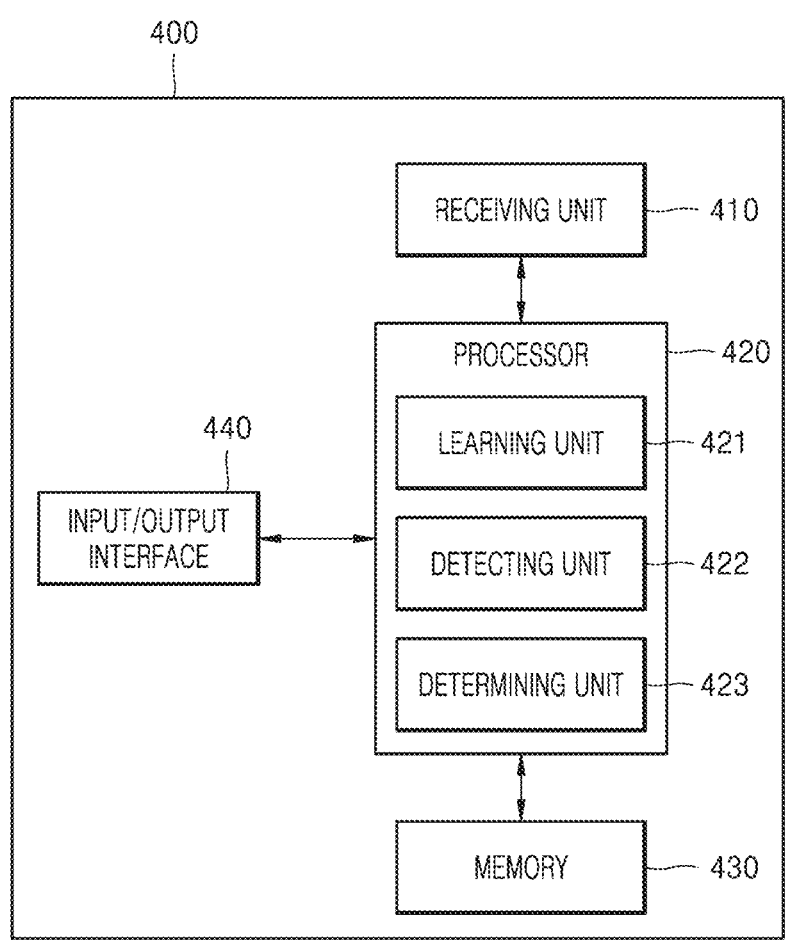
FIG. 3 is a block diagram of an apparatus for providing microorganism information according to an embodiment of the present disclosure.

FIG. 3 illustrates a block diagram of a microorganism information providing apparatus 400 according to an embodiment of the present disclosure.

Referring to FIG. 3, the microorganism information providing apparatus 400 according to an embodiment of the present disclosure may correspond to at least one processor or may include at least one processor. Accordingly, the microorganism information providing apparatus 400 may be driven as in the form included in a hardware device such as a microprocessor or a general-purpose computer system. The term "processor" used herein may refer to a data processing device embedded in hardware, having a physically structured circuit to perform, for example, a function expressed by a code or a command included in a program. As an example of the data processing device embedded in the hardware, there is a processing device such as a microprocessor, a central processing unit (CPU), a processor core, a multiprocessor, an application-specific integrated circuit (ASIC), and a field programmable gate array (FPGA). However, the present disclosure is not limited thereto. The microorganism information providing apparatus 400 may be mounted on at least one of the plurality of user terminals 401, 402, 403, and 404, or may be provided in the server 405. In an embodiment, the microorganism information providing apparatus 400 may be provided in two servers 405. In this case, one of the two servers 405 may learn the microorganism classification criteria to be described below, and the other server may determine the type or concentration of a microorganism in the sample based on the learned algorithm.

The microorganism information providing apparatus 400 illustrated in FIG. 3 illustrates only components related to the present embodiment in order to prevent the features of the present embodiment from being distracted. Therefore, those skilled in the art associated to the present embodiment may understand that other general-purpose elements may be further included in addition to the elements illustrated in FIG. 3.

Referring to FIG. 3, the microorganism information providing apparatus 400 according to an embodiment of the present disclosure may include a receiving unit 410, a processor 420, a memory 430, and an input/output interface 440.

The receiving unit 410 may receive a plurality of images obtained by photographing the outgoing wave L2 emitted from the sample 201 in time series. According to an embodiment, when the microorganism information providing apparatus 400 is mounted on the user terminals 401, 402, 403, and 440 including the image sensor 300, the receiving unit 410 may be connected to the image sensor 300 in a wired manner to receive a plurality of captured images.

According to an embodiment, when microorganism information providing apparatus 400 is included in the server 405 separately provided from the image sensor 300, the receiving unit 410 may function as a communication module using wired or wireless communication to receive a plurality of images. The receiving unit 410 may provide a function for communicating between the user terminal 401 and the server 405 through the network 406. In an embodiment, the receiving unit 410 may provide a function for communicating between the user terminal 401 and another user terminal (for example, the user terminal 402) or another server (for example, the server 405).

For example, a request generated by a processor of the user terminal 401 according to a program code stored in a recording device such as a memory, may be transferred to the server 405 through the network 406 under control of a communication module. Conversely, a control signal, a command, content, a file, or the like provided under the control of the processor 420 of the server 405 may be received by the user equipment 401 through the communication module of the user equipment 401 via the receiving unit 410 and the network 406. For example, a control signal or a command of the server 405 received through the communication module may be transmitted to a processor or a memory.

The processor 420 may be configured to process commands of a computer program by performing basic arithmetic, logic, and input/output computing. The command may be provided to the processor 420 by the memory 430 or the receiving unit 410. For example, the processor 420 may be configured to execute a received command according to a program code stored in a recording device such as the memory 430. The processor 420 may include a learning unit 421, a detecting unit 422, and a determining unit 423.

The memory 430 is a computer-readable recording medium and may include a permanent mass storage device such as a random access memory (RAM), a read only memory (ROM), and a disk drive. Also, the memory 430 may store an operating system and at least one program code (for example, a code for a browser or an application installed and executed in the user terminal 401). The software components may be loaded from a computer-readable recording medium separate from the memory 430 by using a drive mechanism. The separate computer-readable recording medium may include a computer-readable recording medium such as a floppy drive, a disk, a tape, a DVD/CD-ROM drive, and a memory card. In an embodiment, software components may be loaded into the memory 430 through the receiving unit 410, not a computer-readable recording medium. For example, at least one program may be loaded into the memory 430 based on a program (for example, the above-described application) installed by files provided through the network 406 by developers or a file distribution system for distributing an installation file of an application (for example, the above-described server 405).

The input/output interface 440 may be a element for interfacing with an input/output device. For example, an input device may include a device such as a keyboard or a mouse, and an output device may include a device such as a display for displaying a communication session of an application. As another example, the input/output interface 440 may be an element for interfacing with an apparatus in which input and output functions are integrated as one unit, such as a touch screen. In detail, in processing a command of a computer program loaded to the memory 430, the processor 420 of the server 405 may be configured to display a service screen or content configured using data provided by the user terminal 402 on a display through the input/output interface 440.

Hereinafter, the principle of the microorganism information providing apparatus 400 according to the present disclosure will be described with reference to FIG. 4.

Figure 4:
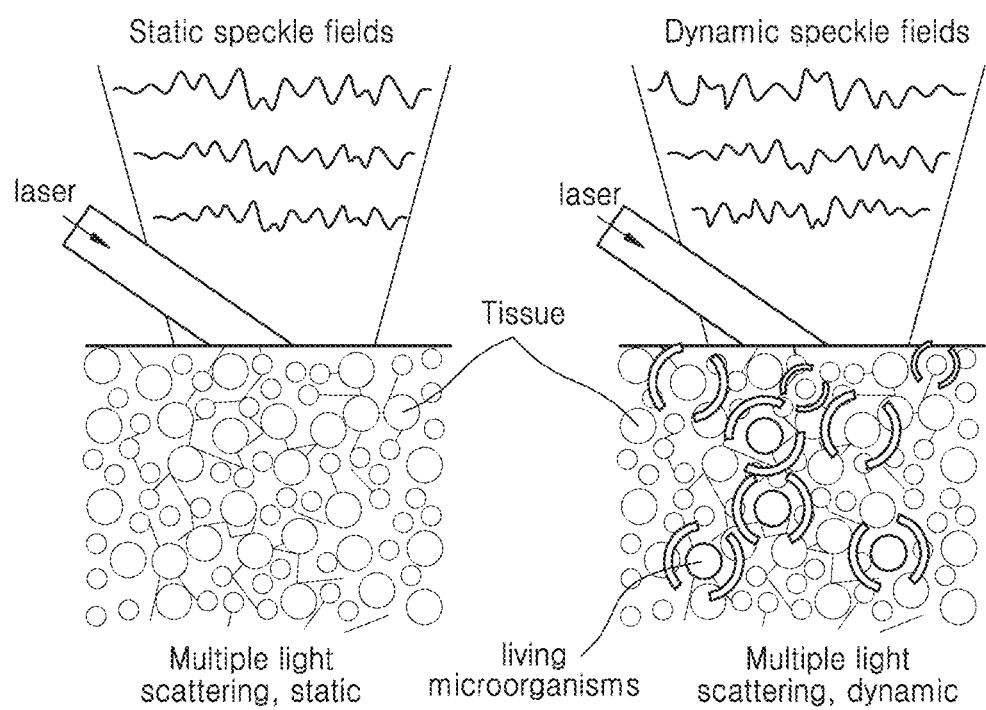
FIG. 4 is a view for explaining a basic principle on how the microorganism information providing apparatus according to an embodiment of the present disclosure confirms the presence of a microorganism in a sample.

FIG. 4 illustrates a diagram illustrating a basic principle of checking the presence of microorganisms in the sample 201 by the microorganism information providing apparatus 400 according to an embodiment of the present disclosure.

In the case of a material having a uniform internal refractive index, such as glass, refraction occurs in a predetermined direction when light is irradiated. However, when a coherent light such as a laser is irradiated onto an object having a non-uniform internal refractive index, a very complex multiple scattering occurs in a material.

Referring to FIG. 4, from among light or waves (hereinafter, referred to as "waves" for simplification) irradiated from a wave source, a portion of waves scattered by multiple scattering along a complicated path may pass through a surface to be inspected. Waves passing through several points of the inspection target surface cause constructive interference or destructive interference, and the constructive/destructive interference of the waves causes a grain-shaped pattern (speckle).

In this specification, waves scattered through such a complicated path are referred to as "chaotic waves", and the chaotic waves may be detected through speckle information.

The left drawing of FIG. 4 illustrates a case where a laser is irradiated into a stable medium. When interference light (for example, a laser) is irradiated into a stable medium having no movement of an internal constituent material, a stable speckle pattern having no change may be observed.

However, as shown in the right drawing of FIG. 4, when there is an unstable medium including an internal constituent material having movement, such as bacteria, or the like, the speckle patterns are changed.

That is, the optical path may be changed in real time due to fine biological activities of living things (for example, intracellular movement, movement of microorganisms, movement of ticks, etc.) Since the speckle pattern is generated due to interference of waves, a fine change in an optical path may cause the change in the speckle pattern. In particular, the small change in an optical path is expressed in a high signal-to-noise ratio due to characteristics of data measured according to embodiments of the present disclosure, which is expressed in an image obtained by interference with a narrow-bandwidth light source, and which is because a signal is affected by a microorganism several times due to multiple-scattering. Accordingly, the movement of the living thing may be rapidly measured by measuring the temporal change of the speckle pattern. As described above, when the change of the speckle pattern over time is measured, the existence and concentration of the living thing may be identified, and the type of living thing may also be identified.

Figure 5A:
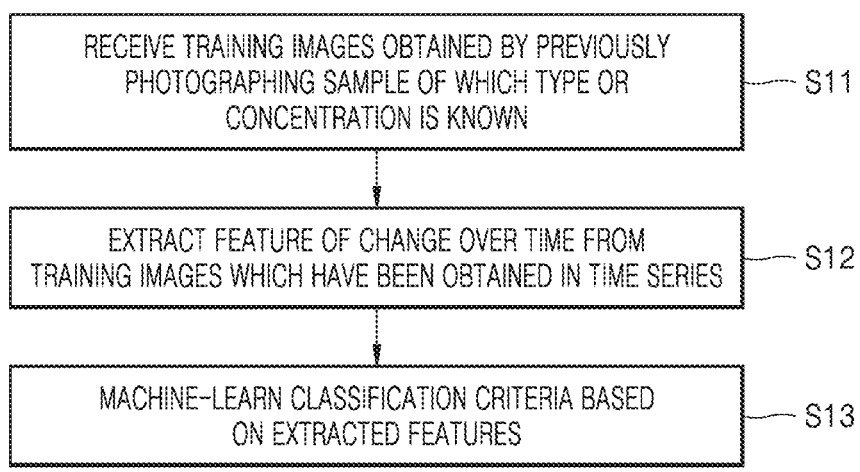
FIGS. 5A and 5B are time-series diagrams illustrating a method of providing microorganism information according to an embodiment of present disclosure.
Figure 5B:
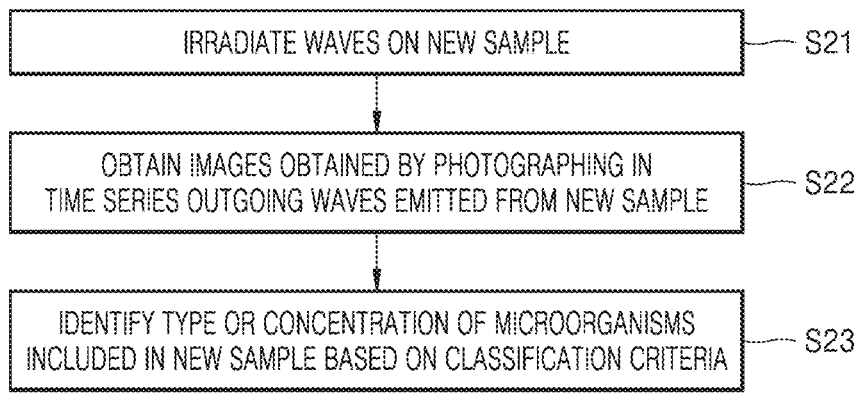

FIGS. 5A and 5B are time-series diagrams illustrating a method of providing microorganism information according to an embodiment of present disclosure; In detail, FIG. 5A illustrates an operation of learning classification criteria in time series in a method of providing microorganism information according to an embodiment of the present disclosure, and FIG. 5B illustrates an operation of classifying a concentration or a type of microorganism based on the classification criteria in the method of providing microorganism information according to an embodiment of the present disclosure.

First, referring to FIG. 5A, in the microorganism information providing system 1 according to an embodiment of the present disclosure, a sample, which has microorganisms of which a type or concentration is known in advance, is prepared, and an image thereof is captured to obtain a plurality of training images.

The process of receiving a plurality of training images in the microorganism information providing system 1 is the same as a process of receiving a plurality of images of a new sample to be described below. In other words, the microorganism information providing system 1 may irradiate the wave L1 to the sample 201 accommodated in the sample unit 200 by using the wave source 100. In this case, the sample 201 may be a sample having a microorganism of which the concentration or type is already known.

Next, the image sensor 300 may capture a plurality of images of the outgoing wave L2 emitted from the sample 201 in time series to obtain the images. In other words, the image sensor 300 may obtain a plurality of images by photographing the sample 201 at a preset time or every time point, and, in this regard, each of the plurality of images may include speckle information generated by multiple scattering caused by microorganisms due to the incident wave L1 entering the sample 201. The image sensor 300 may obtain a plurality of images at such a speed that the movement of microorganisms may be sensed, and, for example, may capture the images of the sample 201 at a speed of 25 to 30 frames per second.

Next, in the microorganism information providing apparatus 400, the receiving unit 410 may receive a plurality of training images obtained by the image sensor 300.

Next, the detecting unit 422 may extract a feature of a change over time from the plurality of training images (S12). Here, the plurality of training images are images which are captured continuously at time intervals, and include time information among the plurality of training images captured in the time series. The detecting unit 422 may extract a feature of a change over time from the plurality of training images.

Next, the learning unit 421 may machine-learns the classification criteria based on the extracted features (S13). The learning unit 421 learns classification criteria based on deep learning, and the deep learning is defined as a set of machine-learning algorithms that attempt to perform a highlevel abstractions (an operation that summarizes core content or functions in a large amount of data or complex data) through a combination of various non-linear conversion schemes. The learning unit 421 may use, for example, any one of a deep neural networks (DNN), a convolutional neural networks (CNN), a reccurent neural network (RNN), and a deep belief networks (DBN) among models of deep learning.

According to an exemplary embodiment, the learning unit 421 may machine-learn the classification criteria based on a temporal correlation among the plurality of received training images.

As described above, the plurality of training images may include information of speckles generated by multiple scattering from the sample 201. As described above with reference to FIG. 4, when microorganisms are present in the sample 201, the speckle may be changed over time due to the biological activity of the microorganisms. In addition, since the change of the speckle over time varies according to the type or concentration of the microorganism, the learning unit 421 may learn classification criteria for classifying the type or concentration of the microorganism by using the change of the speckle according to the time.

According to an embodiment, the learning unit 421 may machine-learn the classification criteria by using a change in a speckle pattern that is speckle information included in each of the plurality of training images, or machine-learn the classification criteria based on the temporal correlation among the plurality of received training images. In this case, the learning unit 421 may learn the classification criteria of the microorganism by using, from among the features, speckle patterns detected from each of the plurality of training images.

Meanwhile, in FIG. 5A, the operation (S12) of extracting the features of the change over time by the detecting unit 422 and the operation (S13) of mechanical-learning the classification criteria based on the features extracted by the learning unit 421 are separately illustrated, but the present disclosure is not necessarily limited thereto, and these operations may be performed simultaneously, not in the order.

Figure 6:
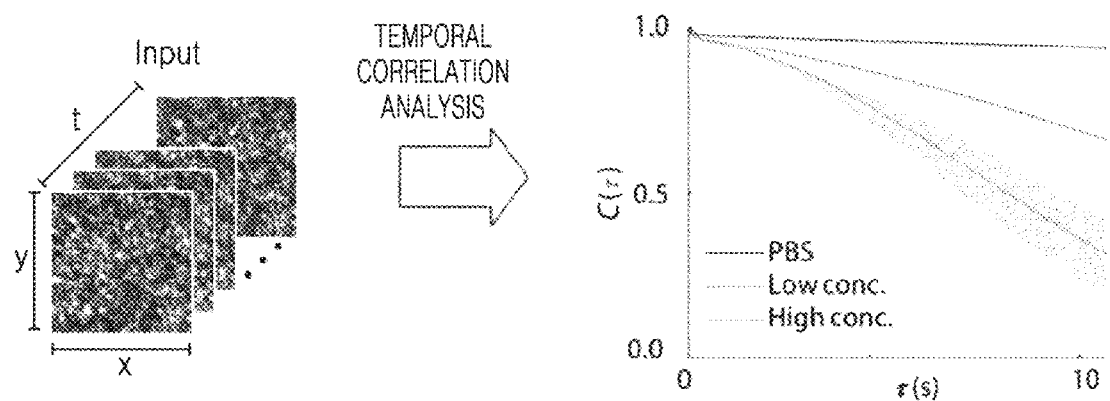
FIG. 6 is a diagram illustrating a method of analyzing a temporal correlation of speckles in a learning unit according to an embodiment of the present disclosure.

FIG. 6 illustrates a diagram illustrating a method of analyzing a time correlation between speckles in the learning unit 421, according to an embodiment.

Referring to FIG. 6, the learning unit 421 may learn the classification criteria by using a difference between first image information of a speckle detected at a first time and second image information of the speckle detected at a second time which is different from the first time. Here, the first image information and the second image information may be at least one of speckle pattern information and wave intensity information. Meanwhile, according to an embodiment of the present disclosure, in addition to the difference between the first image information at the first time and the second image information at the second time, speckle information included in the plurality of images detected at the plurality of times, may also be used. The learning unit 421 may calculate a temporal correlation coefficient among images by using image information of speckles generated at a plurality of preset times, and may learn classification criteria based on the temporal correlation coefficient.

For example, the intensity of light of the speckle pattern calculated based on the intensity of light of the speckle pattern may be calculated by using Equation 3 below.

$$\overline{C}(x, y; \tau) = \frac{1}{T-\tau}\sum_{t=1}^{T-\tau} \overline{I}(x, y; t)\overline{I}(x, y; t+\tau)\delta t \qquad \text{Equation 3}$$

In Equation 3, C denotes a temporal correlation coefficient, I denotes a normalized light intensity, (x, y) denotes a pixel coordinate of a camera, t denotes a measured time, T denotes a total measurement time, and τ denotes a time lag.

The temporal correlation coefficient may be calculated according to Equation 3, and in an embodiment, the learning unit 421 may learn classification criteria for classifying the type or concentration of a microorganism by analyzing that the temporal correlation coefficient is decreased to a preset reference value or lower. In detail, when the temporal correlation coefficient is dropped to a reference value or lower outside a preset error range, it may be confirmed that a microorganism exists, and the reference value may vary depending on the type of a microorganism. The learning unit 421 may learn classification criteria for classifying the types of microorganisms by analyzing the reference values of the temporal correlation coefficient.

Also, as shown in the graph of FIG. 6, as the concentration of microorganisms increases, the temporal correlation coefficient decreases to the reference value or lower more quickly. As such, through the slope value of the graph showing the temporal correlation coefficient, the concentration of microorganisms may be analyzed. The learning unit 421 may learn classification criteria for classifying the concentration of microorganisms by analyzing the slope values of the temporal correlation coefficient.

Figure 7:
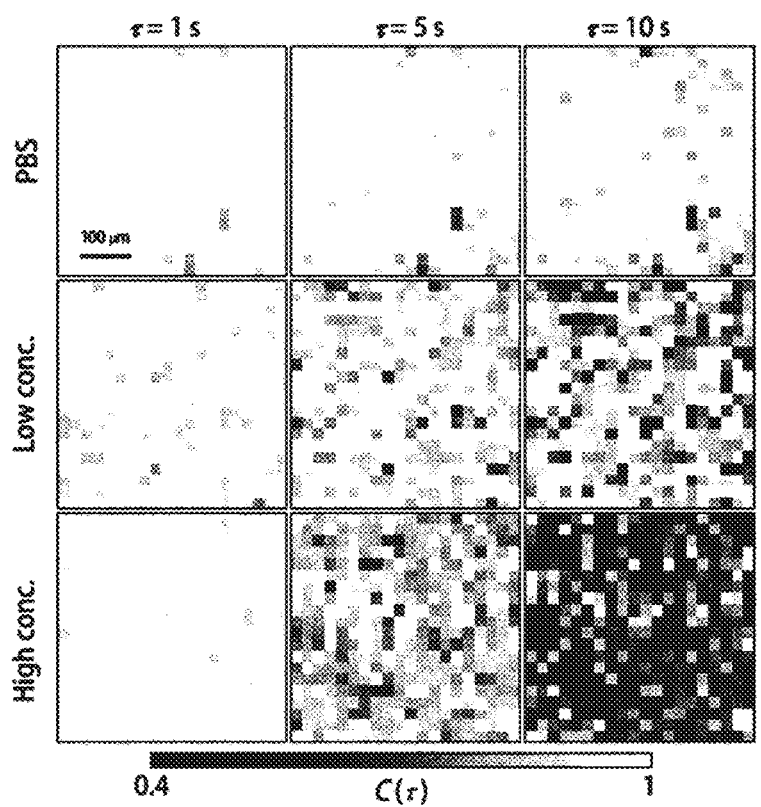
FIG. 7 is a diagram illustrating the distribution of the standard deviation of light intensity of speckles measured over time.

FIG. 7 is a diagram illustrating the distribution of the standard deviation of light intensity of speckles measured over time.

Referring to FIG. 7, the learning unit 421 may calculate a standard deviation of light intensity of a speckle pattern by using a plurality of training images measured at every reference time. As bacteria and microorganisms present in a sample continuously move, constructive interference and destructive interference may change in response to the movement. In this case, as constructive interference and destructive interference are changed, a degree of light intensity may be changed. The learning unit 421 may obtain a standard deviation indicating a degree of change in light intensity, analyze an area in which bacteria and microorganisms exist in the sample, and learn distribution of the bacteria and the microorganisms.

For example, the learning unit 421 may calculate a standard deviation of light intensity over time of a speckle pattern detected from each of the plurality of training images. The standard deviation of light intensity over time of speckle may be calculated based on Equation 4 below.

$$S(x, y) = \sqrt{\frac{1}{T}\sum_{t=1}^{T}(I_t(x, y) - \overline{I})^2} \qquad \text{Equation 4}$$

In Equation 4, S is a standard deviation, (x, y) is a camera pixel coordinate, T is a total measurement time, t is a measurement time, It is a light intensity measured at t time, and I is an average light intensity over time.

The constructive and destructive interference patterns are changed according to the movement of bacteria and microorganisms, and the standard deviation value calculated based on Equation 4 is changed. Accordingly, based on these changes, the concentrations of bacteria and microorganisms may be measured. The learning unit 421 may learn the classification criteria based on a linear relationship between a magnitude of a standard deviation value of the intensity of light of the speckle pattern and the concentration of bacteria and microorganisms.

Hereinafter, a case in which the learning unit 421 learns classification criteria by using a convolutional neural network (CNN) will be mainly described.

Here, the convolutional neural network (CNN) is one of multilayer perceptrons designed to use a minimum amount of preprocessing. The convolutional neural network (CNN) may include a convolution layer to perform convolution with respect to input data, and may further include a subsampling layer to perform subsampling with respect to an image, thereby extracting a feature map from the input data. Herein, the subsampling layer is a layer that increases contrast between neighboring data and reduces an amount of data to be processed, and may be max pooling or average pooling.

Figure 8:
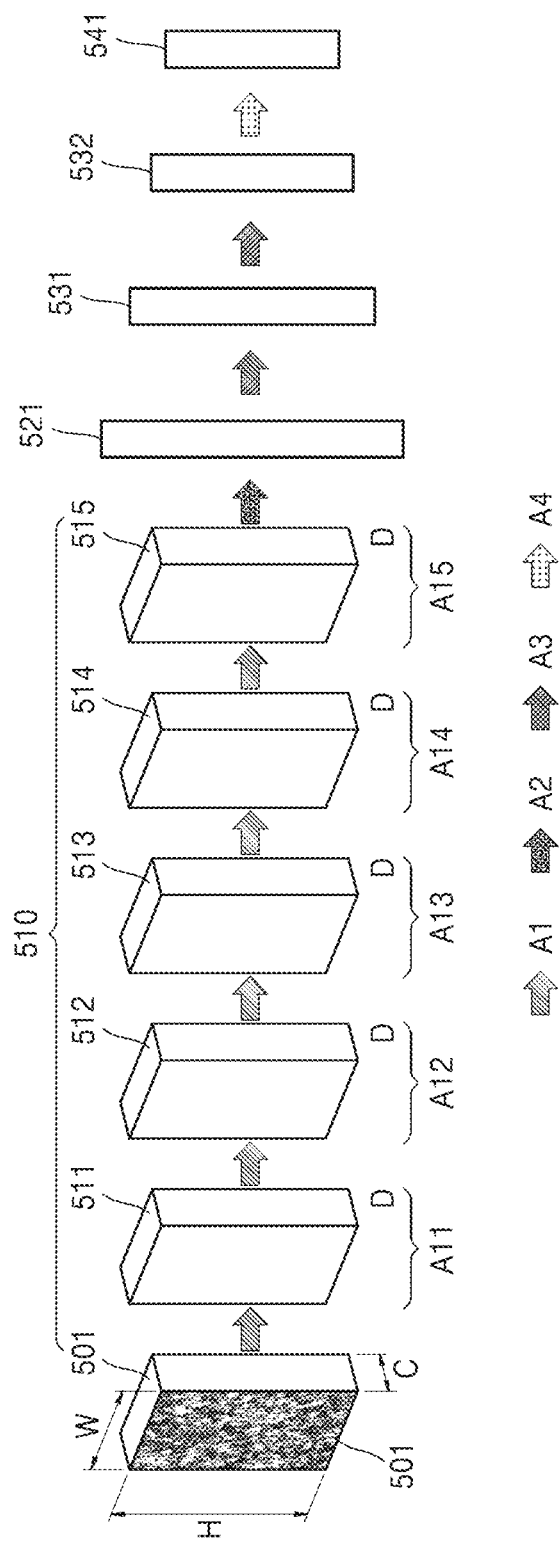
FIG. 8 is a diagram illustrating an example of a convolutional neural network according to an embodiment of the present disclosure.
Figure 9:
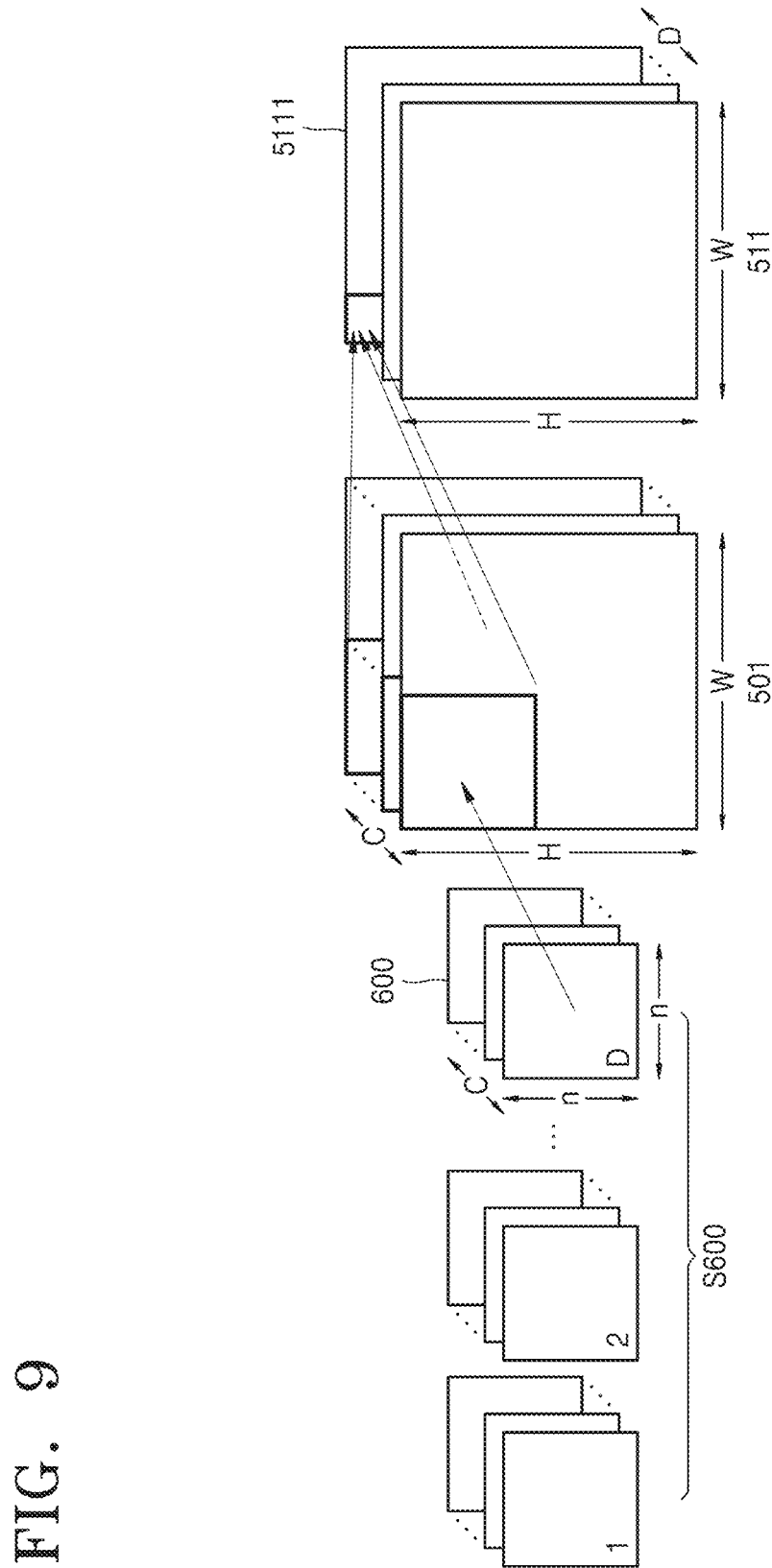
FIGS. 9 and 10 are diagrams for explaining the convolution arithmetic of FIG. 8.
Figure 10:
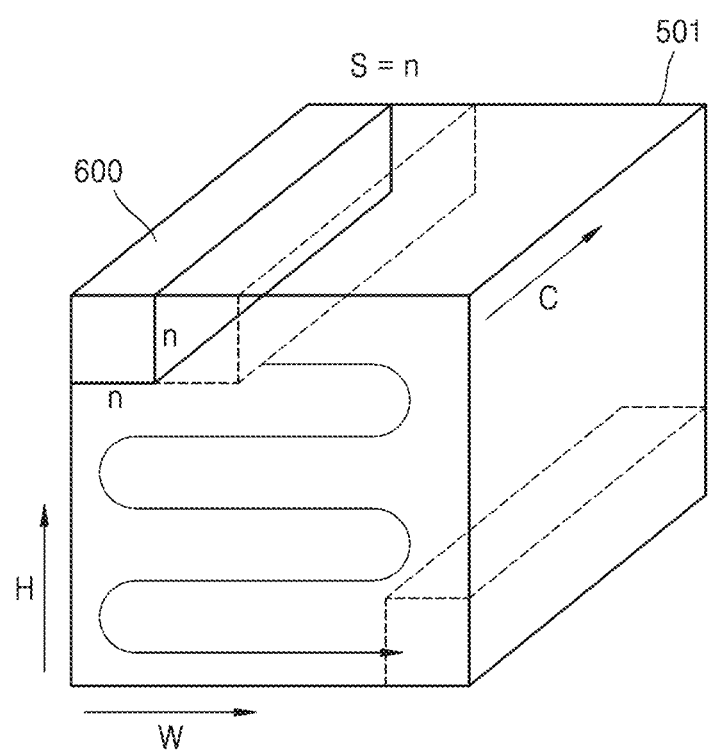

FIG. 8 is an example diagram of a convolutional neural network according to an embodiment of the present disclosure, and FIGS. 9 and 10 are diagrams illustrating convolution arithmetic of FIG. 8.

Referring to FIGS. 8 through 10, a convolutional neural network (CNN) 510 used in the learning unit 421 according to an embodiment may include a plurality of convolution layers A1. The learning unit 421 may generate an output by performing convolution arithmetic between kernels and inputs of convolution layers.

An input of a convolution layer is data employed by an input of the corresponding convolution layer, and includes at least one input feature map corresponding to initial input data or an output generated by a previous layer. For example, an input of a first convolution layer A11 illustrated in FIG. 8 may be a plurality of images that correspond to an input 501 of a convolutional neural network 510, which is the initial input thereof, and an input of a second convolution layer A12 may be an output 511 of the first convolution layer A11.

The input 501 of the convolutional neural network 510 may be a plurality of images 501 in the number of C received by the receiving unit 410, and a temporal correlation may be established among the respective images 501 that are input feature maps. Each image, that is, each input feature map may have a plurality of pixels having a preset width W and a preset height H. Since the number of input feature maps is C, the size of the input 501 may be expressed as W×H×C. The learning unit 421 may perform a convolution arithmetic corresponding to the input 501 by using a single kernel corresponding to the convolution layer A1.

At least one kernel of the convolution layer A1 is data used for a convolution arithmetic corresponding to the convolution layer A1, and may be defined based on, for example, an input and an output of the convolution layer. At least one kernel may be designed for each convolution layer A1 constituting the convolutional neural network 510, and at least one kernel corresponding to each convolution layer may be referred to as a kernel set S600.

The kernel set S600 may include kernels corresponding to output channels D. For example, in order to obtain a desired output of the convolution layer A1, the kernel set S600 of a corresponding convolution layer may be defined such that an input of a corresponding convolutional layer and a convolution arithmetic are performed. An output of the convolution layer A1 is data based on a result of a convolution arithmetic between an input of the corresponding convolution layer and a kernel set, and may include at least one output feature map and be used as an input of a next layer.

The learning unit 421 may generate an output 511 by performing a convolution arithmetic between the input 501 and the kernel set S600 corresponding to the convolution layer A1. The output 511 of the convolution layer A1 may include output feature maps 5111 corresponding to D output channels, and a size of each of the output feature maps 5111 may be W×H. Here, the width, height, and number (depth) of the output 511 may be W, H, and D, respectively, and the size of the output 511 may be expressed as W×H×D.

For example, the kernel set S600 corresponding to the convolution layer A1 may include convolution kernels corresponding to the number of D output channels. The learning unit 421 may generate output feature maps 5111 corresponding to the D output channels based on calculation results between the input 501 and kernels corresponding to the D output channels.

The learning unit 421 may include a plurality of convolution layers A1. In an embodiment, the learning unit 421 may include four to seven convolution layers A1. For example, as illustrated in FIG. 11, five convolution layers A11, A12, A13, A14, and A15 may be included. Through the plurality of convolution layers A11, A12, A13, A14, and A15, the learning capacity of the learning unit 421 which is capable of implying a complicated nonlinear relationship, may be increased. However, the present disclosure is not limited thereto, and the learning may be performed by using more convolution layers A1.

Each of the convolution layers A1 may include an activation function. The activation function may be applied to each layer to perform a function of allowing each input to have a complicated non-linear relationship. As the activation function, a sigmoid function, a tanh function, a rectified linear unit (ReLU), a Leaky ReLU, or the like, which converts an input into a normalized output, may be used.

When the learning unit 421 according to an embodiment of the present disclosure is initially trained by using the convolutional neural network 510, kernels are completely initialized using values of −1 to 1. In this regard, in the case of using an activation function that outputs data having a negative value as 0, output values including valid information cannot be transferred to the next convolution layer, resulting in a decrease in learning efficiency. Therefore, according to an embodiment of the present disclosure, the learning unit 421 may add a Leaky ReLU layer after the convolution layer A1 to output the positive value as it is, but output the negative value input data to have a predetermined gradient. Accordingly, the learning unit 421 may prevent a convergence speed reduction and a local minimization during learning.

The input 501 may be a set of input feature maps to which padding is applied, and padding refers to a technique of filling a partial area of the input with a specific value. In detail, the wording "applying padding to an input while a size of a pad is set to 1" refers to an operation of filling an edge of an input feature map with a specific value, and zero padding refers to setting the specific value to 0. For example, when zero padding in which a size of a pad is 1 is applied to a size input of X×Y×Z, the input, to which the padding, is data in which an edge is 0 and a size is (X+1)×(Y+1)×Z, and may include (X+1)×(Y+1)×Z input elements.

In performing a convolution arithmetic using a plurality of images including speckle information as an input, the learning unit 421 may perform learning using a temporal correlation of the plurality of images. In this regard, each of the plurality of images may include a plurality of speckles which are grain-shaped patterns. In this case, the learning unit 421 may learn the classification criteria based on the temporal correlation of each speckle, and in other words, the learning unit 421 may learn the classification criteria by using 3-dimensional (3D) information including temporal correlation instead of 2-dimentional (2D) information of an image.

The learning unit 421 may concentrate on information about one speckle, and may learn classification criteria by distinguishing the speckle from adjacent speckles in order to accurately obtain 3D information about the speckle. Accordingly, the learning unit 421 may perform a convolution arithmetic using a convolution kernel having a size smaller than the size of one speckle. That is, when the size of one speckle corresponds to m pixels, the learning unit 421 may perform convolution arithmetic using a convolution kernel having the size of n×n smaller than m. According to an embodiment, as described above, since the image sensor 300 is disposed such that up to five pixels are located in a speckle grain size, m may be 5, and in this case, n may have a value of 1. That is, the learning unit 421 may perform convolution arithmetic by using a 1×1 convolution kernel. However, since according to the inventive concept, convolution arithmetic may be performed using a kernel having a size smaller than a size of a speckle, embodiments of the present disclosure are not limited thereto.

The kernel set S600 may include convolution kernels corresponding to the D output channels, and each convolution kernel may include kernel feature maps corresponding to images. Since the size of each kernel feature map is n×n, the kernel set S600 includes n×n×C×D kernel elements. Here, the size of the convolution kernel may be n×n×C, and C may be the number of images, that is, the number of image frames. The number of convolution kernels may be the same as the number (C) of images, and in this case, the convolution kernels may be used for Fourier transform under the same condition using output results of respective layers or analysis using the same.

As illustrated in FIG. 9, the learning unit 421 may generate the output feature maps 5111 corresponding to the first output channel by performing convolution arithmetic between the input 501 and a convolution kernel corresponding to the first output channel in the kernel set S600. In this way, the learning unit 421 may generate the output feature maps 5111 corresponding to the D output channels by performing convolution arithmetic among the D kernels in the kernel set S600 and the input 501, respectively, and may generate the output 511 including the generated output feature maps 5111.

For example, the learning unit 421 performs convolution arithmetic between the convolution kernel 600 corresponding to the D-th output channel having the size of n×n×C and the input 501 having the size of W×H×C to obtain the output feature maps 5111 having the size of W×H, and the generated output feature maps 5111 correspond to the D-th output channel. Specifically, the convolution kernel 600 corresponding to the D-th output channel includes C convolution feature maps, and a size of each kernel feature map is n×n. The learning unit 421, by sliding each kernel feature map having a size of n×n on each input feature map having a size of W×H included in the input 501 to a specific stride, may generate the output feature maps 5111, which is an arithmetic result between the convolution kernel 600 corresponding to the D-th output channel and the input 501.

Here, "stride" refers to a sliding interval of the kernel feature map during a convolution arithmetic. As described above, since the learning unit 421 needs to learn the classification criteria by distinguishing one speckle from adjacent speckles in order to concentrate on information about the speckle, a stride s, which is a sliding interval, may have a value corresponding to the size of a convolution kernel so that each convolution kernel does not overlap an area corresponding to the convolution kernel. In other words, when a convolution kernel having the size of n×n is used, the stride s may have a value of n. For example, in a case of a 1×1 convolution kernel, the stride s may be 1. Accordingly, the learning unit 421 may allow one speckle to non-overlap with other adjacent speckles, and may learn classification criteria by using temporal information about one speckle.

According to an embodiment, in learning the classification criteria using the convolutional neural network 510, the learning unit 421 may perform a convolution arithmetic to have the same number D of output channels as the number C of the plurality of images. In other words, the kernel set S600 may include D convolution kernels including C kernel feature maps, and C and D may be the same.

In an embodiment, the learning unit 421 may reduce the size of the output 515 by performing a pooling operation after a convolution arithmetic using the convolution layers A1. For example, the learning unit 421 may reduce the size of the output 515 using subsampling A2. For example, the subsampling may be a global average pooling which is an operation of setting an average value within a certain range as a representative of a corresponding range. However, the present disclosure is not limited thereto, and max pooling, min pooling, and the like may be used.

Thereafter, the learning unit 421 may, using a fully connected layer, apply a weight together with a certain operation to the feature map 521 extracted by passing through the subsampling filter A2, and then, obtain a final output 541. For example, the learning unit 421 may further apply a leaky ReLU to the fully connected layer after the subsampling A2 is performed (A3), and then apply a softmax layer to the fully connected layer (A4) to obtain the final output. Herein, the final output 541 may be classification criteria for classifying the type or concentration of a microorganism by temporal correlation of the speckle.

Next, referring to FIG. 5B, in the method of providing microorganism information according to an embodiment of the present disclosure, a wave is irradiated on a new sample (S21), and a plurality of images obtained by photographing outgoing waves in time series are received (S22). Thereafter, in the method of providing microorganism information, the type or concentration of a microorganism included in the new sample 201 may be distinguished based on the classification criteria obtained by the determining unit 423 (S23). The output data obtained through the above-described process may be provided to the learning unit 421 again and used as training data.

FIG. 11 is a graph comparing expected microorganism information (prediction) obtained by using a method of providing microorganism information according to an embodiment of the present disclosure with actual microorganism information (ground truth).

Referring to FIG. 11, it can be seen that a matching rate between expected microorganism information obtained by the method of providing microorganism information according to an embodiment of the present disclosure and actual microorganism information is very high. Through the results of FIG. 11, it can be confirmed that according to the method of providing microorganism information, the types of microorganisms (*B. subtilis, E. Coli, P. aeruginosa, S. aureus*) included in the sample 201 and the like are identified, and the respective concentrations are identified.

As described above, the apparatus and method for providing microorganism information according to embodiments of the present disclosure may obtain classification criteria for classifying the type or concentration of a microorganism by using a change in temporal correlation of a speckle. Accordingly, without using a separate chemical method, the type or concentration of a microorganism in a sample can be rapidly and accurately distinguished. Thus, medical treatment such as antibiotics can be rapidly and effectively made on patients with infectious diseases, and various other applications can also be available including checking health conditions of a subject.

Figure 12:
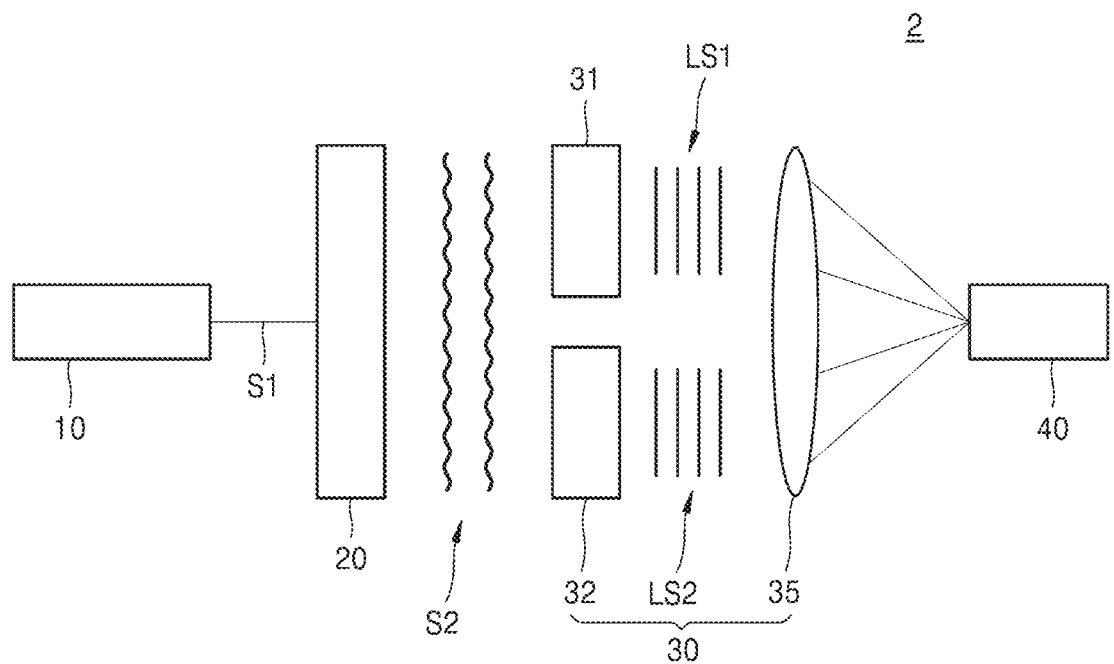
FIG. 12 is a diagram schematically illustrating an optical detection system according to an embodiment of the present disclosure.

FIG. 12 is a diagram schematically illustrating an optical detection system 2 according to an embodiment of the present disclosure.

Referring to FIG. 12, the optical detection system 2 according to an embodiment may include a wave source 10, a sample unit 20, an optical unit 30, and a detecting unit 40.

The wave source 10 may be any type of source devices capable of generating a wave, and may be, for example, a laser capable of irradiating light having a specific wavelength band. The wave source 10 may be connected to a driving device such as a motor or an actuator, and may sequentially irradiate waves toward the sample unit 20 at preset time intervals. The present disclosure is not limited to the type of a wave source, but hereinafter, for convenience of description, a laser will be mainly described.

For example, in order to form a speckle in a sample S accommodated in the sample unit 20, a laser having a good coherence may be used as the wave source 10. In this case, as a spectral bandwidth of a wave source, which determines the coherence of a laser wave source, is reduced, the measurement accuracy may be increased. That is, as a coherence length increases, measurement accuracy may increase. Accordingly, a laser beam, of which the spectral bandwidth is less than the predefined reference bandwidth, may be used as the wave source 10, and the measurement accuracy may be increased as the spectral bandwidth of the wave source is shorter than the reference bandwidth. For example, the spectral bandwidth of the wave source 10 may be set to maintain Equation 1 described above.

According to Equation 1, in order to measure the pattern change of the laser speckle, the spectral bandwidth of the wave source 10 may be maintained to be less than 5 nm when light is irradiated into the sample 20 at every reference time.

Figure 13:
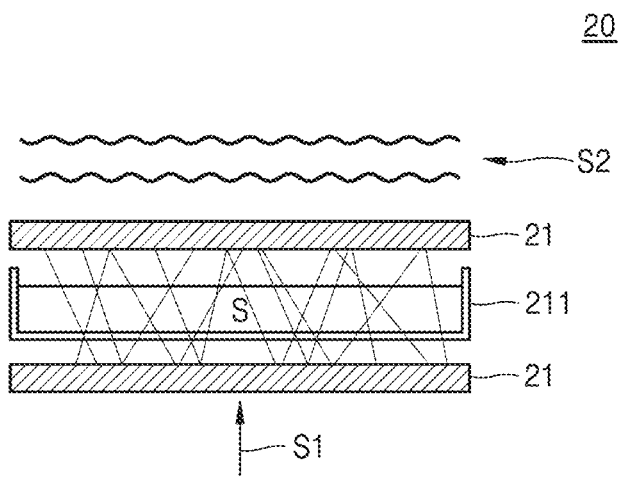
FIGS. 13 and 14 schematically illustrate a sample unit of the optical detection system of FIG. 12.
Figure 14:
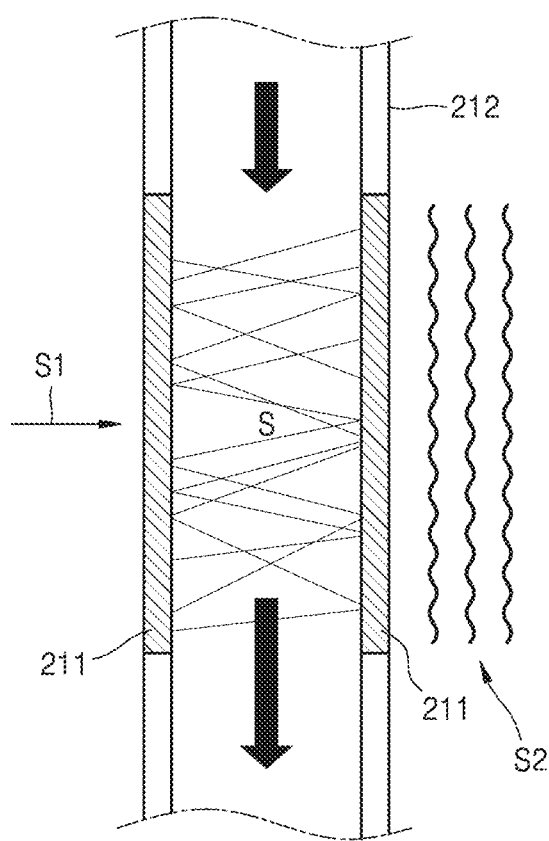

FIGS. 13 and 14 schematically illustrate a sample unit 20 of the optical detection system 2 of FIG. 12.

Referring to FIGS. 12 to 14, the sample unit 20 may accommodate the sample S to be measured. The sample S may be accommodated through a sample placing element such as a container 211 or a pipe 212, and may be accommodated in a static state. According to an embodiment, as illustrated in FIG. 2, the sample unit 20 may contain the sample S stabilized due to no fluidity obtained by using the container 211. According to an embodiment, as illustrated in FIG. 3, the sample unit 20 may contain the sample S having fluidity obtained by using the pipe 212. Here, the sample S may be a liquid, and the sample unit 20 may circulate the sample S one or more times along the entire flow path including the pipe 212 to form the sample S in a stabilized state in the pipe 212.

The sample unit 20 may further include a multiple-scattering amplification unit 21. The multiple-scattering amplification unit 21 may reflect at least a portion of an outgoing wave emitted from the sample S to the sample S to amplify the number of multiple scattering in the sample S. The multiple-scattering amplification unit 21 may include a multiple scattering material. For example, the multiple scattering material may include titanium oxide ($TiO_2$), and the multiple-scattering amplification unit 21 may reflect at least a portion of a wave entering the multiple-scattering amplification unit 21. The multiple-scattering amplification unit 21 may be disposed adjacent to the sample S, and may allow the outgoing wave emitted by being multiple-scattered from the sample S to reciprocate at least once in a space between the sample S and the multiple-scattering amplification unit 21. The multiple-scattering amplification unit 21 may be disposed on the path of the wave, and may be disposed on an area adjacent to incident wave S1 and an area adjacent to outgoing wave S2.

In an embodiment, the optical detection system 2 may be configured such that a multiple scattering material is included in the sample S. In an embodiment, the sample unit 20 may have a multiple scattering amplification area 21 in the main body of the pipe 212. The multiple scattering amplification area 21 may scatter at least a portion of waves which enter the inner space of the pipe 212 and then exit through the sample S, back into the sample S again. The scattered wave is again emitted to the other side through the fluid and scattered, and through this process, the number of multiple scattering in the fluid may be increased. The multiple scattering amplification area 21 may be formed in at least a portion of the path through which the wave passes, for example, in the entire area thereof.

The optical unit 30 may control the wavefront of the outgoing wave S2 and transmit the same to the detecting unit 40. Specifically, the optical unit 30 includes at least one spatial light modulator (SLM) and a lens unit 35 that focuses and transmits the wave emitted from the spatial light modulator to the detecting unit 40.

First and second spatial light modulators 31 and 32 may control a wavefront of a wave scattered in a sample and provide the same to the lens unit 35. The first and second spatial light modulators 31 and 32 may also be referred to as wave shaping devices. The first and second spatial light modulators 31 and 32 may modulate the intensity of waves or simultaneously modulate the intensity and phase of waves. The spatial light modulator 35 may include an instrument or device capable of controlling a wavefront in a desired form in a pixel unit, such as a liquid crystal spatial light modulator (LCSLM), a digital micromirror device (DMD), a deformable mirror (DM), etc.

The optical detection system 2 according to an embodiment may include the first spatial light modulator 31 and the second spatial light modulator 32. In this case, the first spatial light modulator 31 and the second spatial light modulator 32 may be disposed not to overlap each other on a path through which the outgoing wave S2 emitted from the sample unit 20 passes. The first spatial light modulator 31 and the second spatial light modulator 32 may control the wavefront of the outgoing wave S2 at positions thereof.

Here, the first spatial light modulator 31 and the second spatial light modulator 32 may control the outgoing wave S2 emitted from the sample S in a stabilized state in such a way that the controlled wave surface has preset wave surface information.

Hereinafter, a method of detecting an object such as a foreign material or an impurity by controlling a wavefront by the optical unit 30 will be described with reference to FIG. 4.

Figure 15A:
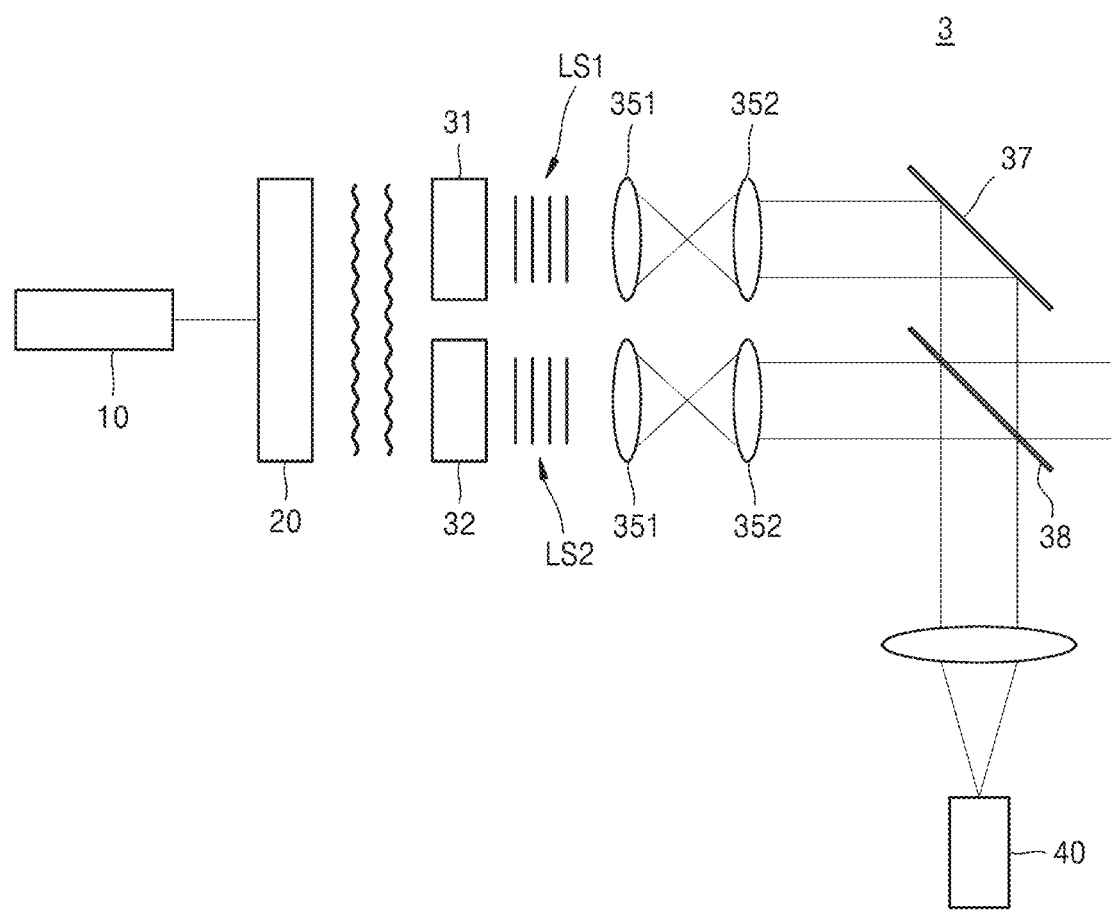
FIGS. 15A and 15B are diagrams for explaining a principle on how an object is detected using an optical detection system according to an embodiment of the present disclosure.
Figure 15B:
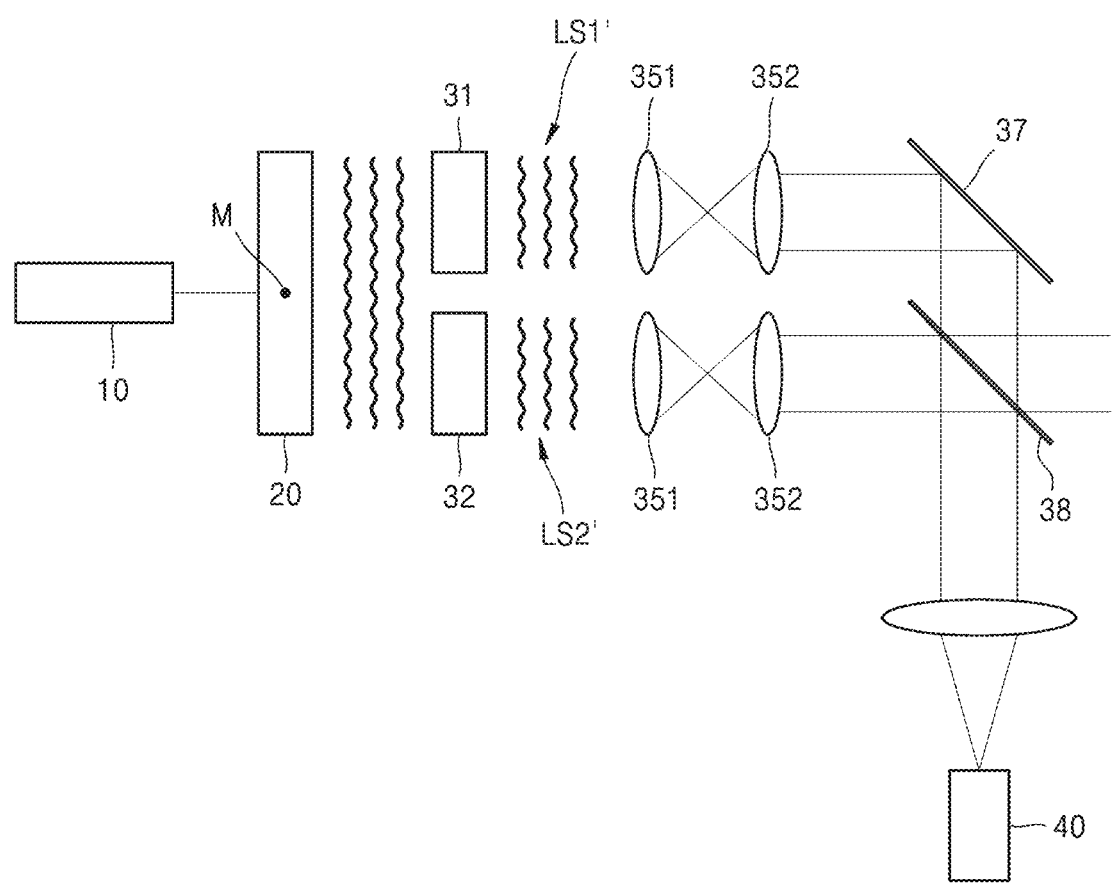

FIGS. 15A and 15B are diagrams for explaining a principle on how an object M is detected using the optical detection system 2 according to an embodiment of the present disclosure.

Referring to FIG. 4, from among incident waves S1 emitted from the wave source 10, a portion of a wave scattered in a complicated path through multiple scattering in the sample unit 20 passes through the surface to be tested. Waves passing through several points of the surface to be tested cause constructive interference or destructive interference, and the constructive/destructive interference of the waves causes a single speckle pattern (speckle). In this case, when the sample is in a stabilized state in which there is no movement of the internal constituent material, a stable speckle pattern having no change when interference light (for example, a laser) is irradiated thereto, may be observed. However, in the case where the internal constituent material includes an unstable medium having movement, such as foreign materials or impurities, for example, bacteria, etc., or in the case where foreign materials or impurities are generated and thus the static state is broken, the speckle pattern may change. That is, the outgoing wave S2 emitted through the sample unit 20 may include sample information having the speckle pattern.

Here, referring to FIG. 15A, in the case where the sample S is in a stabilized state in which the internal constituent material does not move, the first spatial light modulation unit 31 and the second spatial light modulation unit 32 may control the wavefront in such a way that the outgoing wave S2 emitted from the sample unit 20 has a preset intensity and phase. The first spatial light modulator 31 may control the outgoing wave S2 to be a first wave LS1 having first wave information, and the second spatial light modulator 32 may control the outgoing wave S2 to be a second wave LS2 having second wave information. In this case, according to an embodiment, the first wave information and the second wave information may have the same intensity of waves but have phases opposite to each other. This may be expressed by the following Equation 2.

$$I(LS1)=I(LS2)$$

$$P(LS1)=P(LS2)+\pi \quad \text{Equation 2}$$

Herein, I denotes an intensity of waves, and P denotes a phase of waves. Accordingly, in the case where the first wave LS1 and the second wave LS2 are focused by the lens unit 35 when the sample S is in the stabilized state, destructive interference occurs because the first wave LS1 and the second wave LS2 have the same intensity and opposite phases, and ideally, the detecting unit 40, which will be described later, may not sense light as shown in Equation 3.

$$I(LS1+LS2)=0 \quad \text{Equation 3}$$

Referring to FIG. 15B, when the object M such as a foreign material or an impurity is introduced into the sample S, the speckle pattern of the outgoing wave S2 emitted from the sample unit 20 is changed, and when the outgoing wave S2 having the speckle pattern changed while the wavefront is controlled through the above-described configuration is incident on the first spatial light modulator 31 and the second spatial light modulator 32, the outgoing wave S2 is not controlled to have preset wave information. In other words, since the changed first wave LS1 and the changed second wave LS2 have different intensities or different phases, the detecting unit 40 senses light having a certain intensity as shown in Equation 4, unlike Equation 3.

$$I(LS1'+LS2')=kx \quad \text{Equation 4}$$

Here, k may be an amplification constant in the detecting unit 40.

Meanwhile, the lens unit 35 may focus the first wave LS1 and the second wave LS2 emitted from the first spatial light modulator 31 and the second spatial light modulator 32 and provide the focused waves to the detecting unit 40. In this case, the lens unit 35 may include one lens as shown in FIG. 12, or a plurality of lenses 351, 352, and 353 may be disposed in each path as shown in FIGS. 15A and 15B. The lens unit 35 may further include an optical path element such as a mirror 37 or a beam splitter 38 for changing the optical paths of the first wave LS1 and the second wave LS2.

According to an embodiment, the intensity of the first wave LS1 and the intensity of the second wave LS2 controlled by the first spatial light modulator 31 and the second spatial light modulator 32 while the sample S is stabilized may be different from each other. As shown in FIG. 15A or 15B, since the second wave LS2 emitted from the second spatial light modulator 32 is split by the beam splitter 38, the intensity provided to the detecting unit 40 may naturally be less than the first wave LS1. In order to be offset in the detecting unit 40, the first spatial light modulator 31 may control the first wave LS1 such that the intensity of the first wave LS1 is equal to the intensity of the second wave LS2 provided to the detecting unit 40 after passing through the beam splitter 38. Accordingly, the intensity of the first wave LS1 and the intensity of the second wave LS2 before being controlled by the first spatial light modulator 31 and the second spatial light modulator 32 and incident on the lens unit 35, may be different from each other.

The detecting unit 40 may detect focused waves emitted from the optical unit 30 and focused. The detecting unit 40 may be any element that detects a wave. For example, the detecting unit 40 may be a photodiode. As described above, the first wave LS1 and the second wave LS2 emitted from the optical unit 30 are not detected by the detecting unit 40 due to the destructive interference, but when the object M, such as a foreign material or an impurity, enters the sample S, a wave (light) may be directly detected.

According to an embodiment, the detecting unit 40 may further include an optical fiber to receive the first wave LS1 and the second wave LS2 from the optical unit 30. The optical fiber may be a single mode optical fiber. The first wave LS1 and the second wave LS2 may perform a single mode filtering by passing through a single mode fiber. Here, instead of the single mode optical fiber, a single mode pin hole having a size equal to or smaller than an optical focus size may be used.

Figure 16:
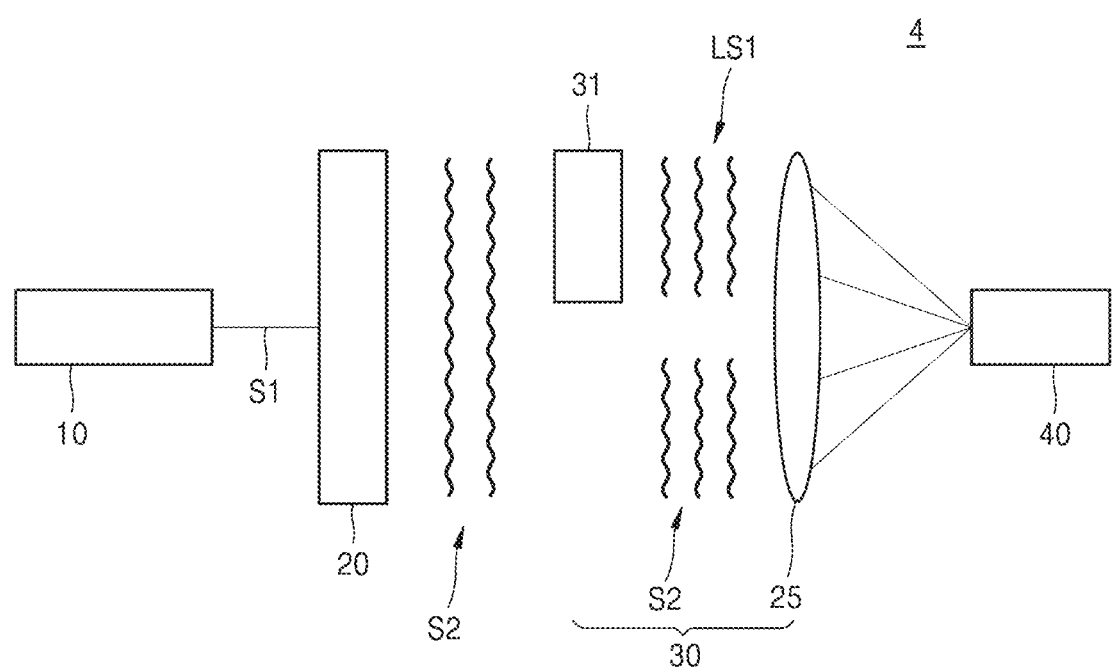
FIG. 16 is a diagram schematically illustrating an optical detection system according to an embodiment of the present disclosure.

FIG. 16 is a diagram schematically illustrating an optical detection system 4 according to an embodiment of the present disclosure.

Referring to FIG. 16, the optical detection system 4 according to another embodiment may include the wave source 10, the sample unit 20, the optical unit 30, and the detecting unit 40. The optical detection system 4 according to the present embodiment is the same as the optical detection system 2 of the previous embodiment except for the configuration of the optical unit 30. Accordingly, the same description will be omitted for convenience of description.

The optical unit 30 according to another embodiment may include only the first spatial light modulator 31. The first spatial light modulator 31 may control the outgoing wave S2 to convert the outgoing wave S2 into the first wave LS1. In this case, the optical unit 30 may provide, as the second wave LS2, a portion of the outgoing wave S2 as it is to the lens unit 35. In other words, the optical unit 30 may use a portion of the outgoing wave S2 as the second wave LS2, and control the other portion of the outgoing wave S2 to cause destructive interference to occur with the second wave LS2, thereby performing the same function as the previous embodiment.

As described above, an optical detection system according to the embodiments of the present disclosure may divide the wave emitted from the sample into a first wave and a second wave, and control the intensity and phase of at least one of the first and second waves by using a SLM so that the first and second waves destructively interfere with each other in the detecting unit 40. Accordingly, the optical detection system according to the embodiments of the present disclosure can detect the presence of an impurity such as a microorganism in a sample by only detecting whether waves are present in the detecting unit. In addition, the optical detection system according to the embodiments of the present disclosure can immediately recognize the presence of impurities through the presence or absence of waves. Accordingly, even when a very small amount of impurities are present, sensitive detection is possible.

Hereinbefore, the present disclosure has been described using embodiments. It will be appreciated by those skilled in the art that the present disclosure can be implemented in a modified form in a range that does not deviate from the essential characteristics of the present disclosure. Therefore, the disclosed embodiments should be considered in terms of explanation, not in a limited aspect. The scope of the present disclosure is not described above, but is shown in the claims, and all differences within the scope of the present disclosure should be construed as being included in the present disclosure.

INDUSTRIAL AVAILABILITY

According to an embodiment of the present disclosure, an apparatus for providing microorganism information is provided. Also, embodiments of the present disclosure may be applied to an apparatus for detecting impurities or microorganisms, which are used for industrial purposes.

What is claimed is:

1. An apparatus for providing microorganism information, the apparatus comprising:
   a receiving unit configured to receive a plurality of images obtained by photographing in time series an outgoing wave emitted from a sample;
   a detecting unit configured to extract a feature of a change over time from the plurality of images obtained in time series;
   a learning unit configured to machine-learn classification criteria based on an extracted feature; and
   a determining unit configured to classify the type or concentration of a microorganism contained in the sample based on the classification criteria, wherein
   each of the plurality of images includes speckle information generated by multiple scattering caused by the microorganism due to a wave entering into the sample,
   wherein the learning unit learns the classification criteria by using a convolutional neural network (CNN), and
   wherein the learning unit performs a convolution arithmetic by using a convolution kernel having a size smaller than a size of one speckle.

2. The apparatus of claim 1, wherein
   the learning unit performs a convolution arithmetic by using a convolution kernel having a size of n×n smaller than m when a size of one speckle corresponds to m pixels.

3. The apparatus of claim 2, wherein
   a stride of the convolution arithmetic corresponds to the value n.

4. The apparatus of claim 2, wherein
   the convolution kernel comprises kernel feature maps corresponding to or greater than the number of the plurality of images.

5. The apparatus of claim 4, wherein
   the learning unit performs a convolution arithmetic by using a kernel set including a plurality of convolution kernels corresponding to the number of output channels.

6. The apparatus of claim 5, wherein
   the number of output channels by the convolution arithmetic corresponds to the number of the plurality of images.

7. The apparatus of claim 1, wherein
   the classification criteria is learned by using one of a change in a shape of a speckle pattern in the feature, a temporal correlation coefficient calculated based on an intensity of light of the speckle pattern, and a change in a standard deviation value of the intensity of light of the speckle pattern.

8. The apparatus of claim 7, wherein
   the standard deviation value and the concentration of the microorganism has a linear relationship.

9. An apparatus for providing impurity information, the apparatus comprising:
   a receiving unit configured to receive a plurality of images obtained by photographing in time series an outgoing wave emitted from a sample;
   a detecting unit configured to extract a feature of a change over time from the plurality of images obtained in time series;
   a learning unit configured to machine-learn classification criteria based on an extracted feature; and
   a determining unit configured to classify the type or concentration of an impurity contained in the sample based on the classification criteria, wherein
   each of the plurality of images includes speckle information generated by multiple scattering caused by the impurity due to a wave entering into the sample, and
   the learning unit is configured to distinguish one speckle from surrounding speckles in the plurality of images and to learn the classification criteria using time information of the one speckle.

10. A method of providing microorganism information, the method comprising:
   receiving a plurality of training images which have been obtained by photographing in time series an outgoing wave emitted by irradiating a wave to a sample containing a microorganism of which type or concentration is previously known;
   machine-learning classification criteria based on a feature of a change over time from the plurality of training images which have been obtained in time series;
   receiving a plurality of images obtained by photographing in time series an outgoing wave which is emitted by irradiating a wave onto a new sample; and
   identifying a type or a concentration of a microorganism included in the new sample based on the plurality of images and the classification criteria, wherein
   each of the plurality of training images or each of the plurality of images comprises speckle information that is generated by multiple scattering by the microorganism due to waves incident on the sample or the new sample, wherein the machine-learning of the classification criteria comprises learning the classification criteria by using a convolutional neural network (CNN) and performing a convolution arithmetic by using a convolution kernel having a size smaller than a size of one speckle.

11. The method of claim 10, wherein the machine-learning of the classification criteria comprises performing a convolution arithmetic by using a convolution kernel having a size of n×n smaller than m when a size of one speckle corresponds to m pixels.

12. The method of claim 11, wherein a stride of the convolution arithmetic corresponds to the value n.

13. The method of claim 10, wherein the convolution kernel comprises kernel feature maps corresponding to or greater than the number of the plurality of images.

14. The method of claim 13, wherein the machine-learning of the classification criteria comprises performing a convolution arithmetic by using a kernel set including a plurality of convolution kernels corresponding to the number of output channels.

15. The method of claim 14, wherein the number of output channels by the convolution arithmetic corresponds to the number of the plurality of images.

16. The method of claim 10, wherein the learning unit learns the classification criteria based on temporal correlation of the plurality of images.

* * * * *